United States Patent [19]
Templeton et al.

[11] Patent Number: 6,114,118
[45] Date of Patent: Sep. 5, 2000

[54] METHOD OF IDENTIFICATION OF ANIMALS RESISTANT OR SUSCEPTIBLE TO DISEASE SUCH AS RUMINANT BRUCELLOSIS, TUBERCULOSIS, PARATUBERCULOSIS AND SALMONELLOSIS

[75] Inventors: Joe W. Templeton; Jianwei Feng; L. Garry Adams, all of College Station, Tex.; Erwin Schurr; Philippe Gros, both of Montreal, Canada; Donald S. Davis; Roger Smith, III, both of College Station, Tex.

[73] Assignees: Texas A&M University System, College Station, Tex.; McGill University, Montreal, Canada

[21] Appl. No.: 08/903,139

[22] Filed: Jul. 30, 1997

Related U.S. Application Data

[60] Provisional application No. 60/031,443, Sep. 20, 1996.

[51] Int. Cl.$^7$ .............................. C12Q 1/68; C12P 19/34
[52] U.S. Cl. ............................................. 435/6; 435/91.2
[58] Field of Search ....................... 435/6, 91.2; 935/77, 935/78

[56] References Cited

U.S. PATENT DOCUMENTS

| | | | |
|---|---|---|---|
| 4,385,535 | 5/1983 | Falkow et al. | 435/5 |
| 5,190,860 | 3/1993 | Adams et al. | 435/7.32 |
| 5,763,168 | 6/1998 | Lalouel et al. | 435/6 |

FOREIGN PATENT DOCUMENTS

| | | |
|---|---|---|
| WO94/20641 | 9/1994 | WIPO . |
| WO95/13371 | 5/1995 | WIPO . |
| WO96/35793 | 11/1996 | WIPO . |

OTHER PUBLICATIONS

Alonso et al. Electrophoresis 17:12990–1301 1996.
Mullis, Cold Spring Harbor L1: 263–273 1986.
Genebank Sequence Alignments (seq ID No. 11).
Genbank Sequence Alingment (seq ID No. 12).
Adams et al. Proceedings Annual Meeting of US Animal Health Assoc. 99:111–116 (Abstract) 1995.
Malo et al Animal Biotechnology 5(2): 173–182 1994.
Bishop, Michael D. et al., "A Genetic Linkage Map for Cattle", *Genetics*, 136:619–639 (Feb., 1994).
Feng, Jianwei, "Bovine Natural Resistance Associated Macrophage Protein 1 (Nrampl1) Gene", *Genome Research*, 6:956–964 (1996).
Qureshi, T. et al., "Intracellular Survival of *Brucella abortus*, *Mycobacterium Bovis* BCG, *Salmonella dublin*, and *Salmonella typhimurium* in Macrophages from Cattle Genetically Resistant to *Brucella abortus*", *Vet. Immunology and Immunopathylogy*, 50 (1996) 55–65.
Adkison, L. R. et al. "Somatic Cell Mapping and Restriction Fragment Analysis of Bovine Alpha and Beta Interferon Gene Famlies" *Cytogenet. Cell Genet.* 47:62–65 (1988).
Barton, C.H., et al. "NH2–terinal Sequence of Macrophage–Expressed Natural Resistance–associated Macrophage Protein (Nramp) Encodes a Proline/Serine–rich Putative Src homology 3–binding Domain" *J. Exp. Med* 179:1683–1687 (1994).

Beever, J. E. et al. "A Genetic Map of nine Loci on Bovine Chromosome 2" *Mamm. Gen.* 5:542–545 (1994).
Blackwell, J. M. et al. "Genetic Regulation of Leishmanial and Mycobacterial Infections: the lsh/Ity/Bcg Gene Story Continues" *Immunol. Lett.* 43:99–107 (1994).
Blackwell, J. et al. "Genetic Regulation of Macrophage Primming/Activation: the Lsh Gene Story" *Immunol. Lett.* 30:241–248 (1991).
Blower, Sally M., et al. "The Intrinsic Transmission dynamics of Tuberculosis Epidemics", *Nature Medicine*, 1(8);815–821 (1995).
Cameron, H.S. et al. "Genetic Resistance to Bruclelosis in Swine" *J. Anim. Sci.* 1:106–110 (1942).
Cameron, H. S. et al. "Studies on Genetic Resistance in Swine to Brucella Infection: Preliminary Report" *Cornell Vet.* 30:218–222 (1940).
Campbell, G. A. et al. "The Long–term Culture of Bovine Monocyte–derived Macrophages and their Use in the Study of Intracellular Proliferation of *Brucella abortus*" *Vet Immunol. Immunopathol.* 34: 291–305 (1992).
Cellier, M. et al. "Human Natural Resistance–associated Macrophage Protein: cDNA Cloning, Chromosomal Mapping, Genomic Organization, and Tissue–specific Expression" *J. Exp. Med* 180:1741–1752 (1994).
Cerretti, D. P. et al. "The Mruine Hojmolog of the Human Interleukin–8 Receptor Type B Maps Near the Ity/Lsh/Bcg Disease Resistance Locus" Genomics 18:410–413 (1993).
Chirgwin, J. M. et al. "Isolation of Biologically Acive Ribnucleic Acid from Sources Enriched in Ribonuclease" *Biochemistry* 18:5294–5299 (1979).
deChastellier C. et al. "Implication of Phagosomelysosome Fusion in Restriction of Mycobacterium avium Growth in Bone Marrow Macrphages from Genetically Resistant Mice" *Infec. Immun.* 61:3775–3784 (1993).
Dietrich, R. A. et al. "Economic and Epidemiologic Analysis of U.S. Bovine Brucellosis Programs. Primary Report" Texas A&M University, College Station, Texas vol. I, p. 1–24 (1986).

(List continued on next page.)

*Primary Examiner*—Eggerton A. Campbell
*Attorney, Agent, or Firm*—Fulbright & Jaworski L.L.P.

[57] ABSTRACT

The present invention relates to materials and methods for identifying animals that are resistant or susceptible to diseases associated with intracellular parasites such as brucellosis, tuberculosis, paratuberculosis and salmonellosis. More particularly, the present invention relates to the identification of a gene, called NRAMP1, which is associated with the susceptibility or resistance of an animal, such as an artiodactyla to diseases such as brucellosis, tuberculosis, paratuberculosis and salmonellosis. Still more particularly, the present invention relates to the identification of specific sequences of bovine NRAMP1 which associate with resistance or susceptibility to ruminant brucellosis, tuberculosis, paratuberculosis and salmonellosis, and to the method of identifying said sequences to identify animals who are susceptible or resistant to disease.

44 Claims, 21 Drawing Sheets

OTHER PUBLICATIONS

Dosik, J.K. et al. "An Nramp–related Sequence Maps to Mouse Chromosome 17" *Mamm. Gen.* 5:458–460 (1994).

el–Gazzar, F. E. et al. "Salmonellellae, Salmonellosis, and Dairy Foods: A Review" *J. Dairy Sci.* 75:2327–43 (1992).

Essey, M.A. "Bovine Tuberculosis Eradication: A National Challenge" *In Proc. of the 12th Annual World Assoc. of Vet. Microbiologists, Immunologits, and Specialists in Infectious Diseases,* University of California, David CA B. Osburn (Ed.) p. 38–46.

Essey, M.A. et al. "Status of Bovine Tuberculosis in North America" *Vet. Microbiol.* 40:15–22 (1994).

Feinberg, A. P. et al. "A Technique for Radiolabeling DNA Restriction Endonuclease Fragments to High Specific Activity" *Anal. Biochem.* 132:6–13 (1983).

Frelier, P.F. et al. "Genetic Regulation of *Mycobacterium paratuberculosis* infection in Recombinaint Inbred Mice" *Vet. Pathol.* 17:362–364 (1990).

Fries, R. et al. "The Bovine Genome Mapping Project" *Mamm. Gen.* 4:405–428 (1993).

Goto, Y. et al. "Regulation of Host Resistance to Mycobacterium Intracellular in vivo and in vitro by Bcg Gene" *Immunogenetics* 30:218–221 (1989).

Gros, P. et al. "Cellular Mechanisms of Genetically Controlled Host Resistance to *Mycobacterium bovis* (BCG)" *J. Immunol.* 131:1966–1972 (1983).

Gruenheid, S. et al. "Identification and Characterization of a Second Mouse Nramp Gene" *Genomics* 25:99–107 (1995).

Harmon, B. G. et al. In "Genetic Control of Host Resistance to Infection and Malignancy", E. Skamene (Ed.) Alan R. Liss, Inc., New York, pp. 345–354 (1985).

Harmon, B. G. et al. "Macrophage Function in Mammary Glands of *Brucella abortus*–Infected Cows and Cows that Resisted Infection After Inoculation of *Brucella abortus*" *Am. J. Res.* 50:459–465 (1989).

Ivanyi, J. "Molecular Biology of Natural Disease Resistance–Associated Macrophage Protein" *Parasitol. Today* 10:416–417 (1994).

Kramnik, I., et al. "T–helper 1–like Subset Selection in Mycobacterium bovis bacillus Calmette–Guerin–Infected Resistant and Susceptible Mice" *Immunology* 81:618–625 (1994).

Lim, W. A. et al. "Critical Residues inan SH3 Domain from Sem–1 Suggests a Mechanisms for Proline–Rich Peptide" Nature Structural Biology 1:221–225 (1994).

Malo, D. et al. "Genetic Control of Host Resistance to Infection" *TIG* 10:365–371 (1994).

Martin, S. W. et al. "Livestock Disease Eradication: Evaluation of the Cooperative State–Federal Bovine Tuberculosis Eradication Program" National Research Council, Washington, D.C. p. 1–97 (1994).

Mock, B. et al. "A Genetic Map of Mouse Chromosome 1 Near the Lsh–Ity–Bcg Disease Resistance Locus" *Genomics* 7:57–64 (1990).

Musacchio, A. et al. "High–resolution Crystal Structures of tyrosine Kinase SH3 Domains Complexed with Proline–Rich Peptides" *Nature Struct. Biol.* 1:546–551 (1994).

Nathan, C. "Natural Resistance and Nitric Oxide" *Cell* 82:873–876 (1995).

Plant, J. E. et al. "Are the Lsh and Ity Disease Resistance Genes at One Locus on Mouse Chromosome 1" *Nature* 297:510–511 (1982).

Price, R.E. et al. "Ability of Mononuclear Phagocytes from Cattle Naturally Resistant or Susceptible to Brucellosis to Control in vitro Intracellular Survival of *Brucella abortus*" *Infect. Immun.* 58:879–886 (1990).

Qureshi, T. et al. "Intracellular Survival of *Brucella abortus, Mycobacterium bovis* (BCG), *Salmonella dublin* and *Salmonella typhimurium* in Macrophages from Cattle Genetically Resistant to *Brucella abortus*" *Veterinary Immunology and Immunopathology* 50:55–56 (1996).

Radzioch, D. et al. "Genetic Resistance/Susceptibility to Mycobacteria:Phenotypic Expression in Bone Marrow Derived Macrophage Lines" *J. Leukoc. Bio.* 50:263–271 (1991).

Roach, T.I.A. et al. "Induction of Early–Response Genes KC and JE by Mycobacterial Lipoarabinomannans: Regulation of KC Expression in Murine Macrophgaes by Lsh/Ity/Bcg (Candidate Nramp)" *Infect. Immun.* 62:1176–1184 (1994).

Roach, T.I.A. et al. "Role of Inorganic Nitrogen Oxides and Tumor Necrosis Factor Alpha in Killing Leishmania donovani Amastigotes in Gamma Interferon–Lipopolysaccharide–activated Macrophages from $Lsh^s$ and $Lsh^r$ Congenic Mouse Strains" *Infect. Immun.* 59:3935–3944 (1991).

Sanger, F. et al. "DNA Sequencing with Chain Termination Inhibitors" *Proc. Natl. Acad. Sci* USA 74:5463–5467 (1977).

Schurr, E. et al. "Genetic Control of Innate Resistance to Mycobacterial Infections" *Immunol. Today* 12:A42–A45 (1991).

Skamene, E. et al. "Regulation of Resistance to Leprosy by Chromosome 1 Locus in the Mouse" *Immunogenetics* 19:117–124 (1984).

Skow, L.C. et al. "Mapping of the Mouse Fibronectin Gene (Fn–1) to Chromosome 1: Conservation of the Idh–1–Cryg–Fn–1 Synteny Group in Mammals" *Genomics* 1:283–286 (1987).

Templeton, J. W. et al. In Advances in Brucellosis Research, L.G. Adams (Ed.) Texas A&M University Press, College Station, 144–150 (1990).

Templeton, J. W. et al. "Genetics of Natural Resistance to Tuberculosis" In Tuberculosis in Wildlife and Domestic Animals, F. Griffin and G. de Lisle (Eds.) University of Otago, Dunnedin, New Zealand, 29–32 (1996).

Templeton, J. W. et al. "Immunogenetics of Natural Resistance to Bovine Brucellosis" *4th World Cong. Genetics Applied to Livestock Production,* 396–399 (1990).

Templeton, J. W. et al. "Natural Disease Resistance in Domestic Animals" *J. Am. Vet. Med. Assoc.* 192:1306–1315 (1988).

Tietjen, M. et al. "Salmonellae and Food Safety" Crit. Rev. Microbiol. 21:53–83 (1995).

Vidal, S. M. et al. "Natural Resistance to infection with Intracellular Parasites: Isolation of a Candidate for Bcg" *Cell* 73:469–485 (1993).

White, J. K. et al. "Genetic and Physical Mapping 2q35 in the Region of the NRAMP and IL8R Genes: Identification of a Polymorphic Repeat in the Exon 2 of NRAMP" *Genomics* 24:295–302 (1994).

Womack, J. E. et al. "Chromosomal Evolution from the Perspective of the Bovine Gene Map" *Anim. Biotech* 5:123–128 (1994).

Womack, J.E. et al. "Gene Map of the Cow: Conservation of Linkage with Mouse and Man" *J. Hered.* 77:2–7 (1986).

Young, Clarence L., et al. "Calcium Regulation of Actin Filament Capping and Monomer Bidning by Macrophage Capping Protein", J. Bio. Chem., 269 (19):13997–14002 (1994).

Yu, H. et al. "Structural Basis for the Binding of Proline–Rich Peptides to SH3 Domains" *Cell* 76:933–945 (1994).

Sequences of Primers used In SSCA and/or SSCP Analysis

SEQ ID NO; 1
Fmicro1     5'    AAGGCAGCAA GACAGACAGG    3'

SEQ ID NO: 2
3end3       5'    ATGGAACTCA CGTTGGCTG     3'

FIG. 1A

Sequences of Primers used to Clone Bovine NRAMP1

SEQ ID NO: 3
murine 1F primer   5'    TCTCTGGCTG AAGGCTCTCC    3'

SEQ ID NO: 4
murine 1R primer   5'    CCAAGCTCAC CTTAGGGTAG    3'

SEQ ID NO: 5
PE2 primer         5'    CGTGGTGACA GGCAAGGAC     3'

SEQ ID NO: 6
Mut2 primer        5'    CCAAGAAGAG GAAGAAGAAG GTGTC    3'

FIG. 1B

```
                                                                                     pts
                                                                                      |
SEQ ID NO. 7  NRAMP1      MtGDkGPqrl  sGssYGSISS  PtSPgPQQAP  PreTYLSEKI  PIPDTkpGTF>
SEQ ID NO. 8  Nramp1      MisDksPPrl  srpsYGSISS  lPgPaPQpAP  creTYLSEKI  PIPsadqGTF>
SEQ ID NO. 9  BovNramp1   MSGDTGPPKQ  GGTRYGSISS  PPSPEPQQAP  PGGTYLSEKI  PIPDTESGTF  50
                                                                                      PKC
              NRAMP1      SLRKLWAFTG  PGFLMSIAFL  DPGNIESDLQ  AGAVAGFKLL  WVLLWATVLG>
              Nramp1      SLRKLWAFTG  PGFLMSIAFL  DPGNIESDLQ  AGAVAGFKLL  WVLLWATVLG>
              BovNramp1   SLRKLWAFTG  PGFLMSIAFL  DPGNIESDLQ  AGAVAGFKLL  WVLLWATVLG  100
                          PKC         TM1                                 TM2

NRAMP1      LLCQRLAARL  GVVTGKDLGE  VCHcYYPKVP  RtvlWLTIEL  AIVGSDMQEV>
              Nramp1      LLCQRLAARL  GVVTGKDLGE  VCHLYYPKVP  RILLWLTIEL  AIVGSDMQEV>
              BovNramp1   LLCQRLAARL  GVVTGKDLGE  VCHLYYPKVP  RILLWLTIEL  AIVGSDMQEV  150
                                                                          TM3

NRAMP1      IGTAIAFnLL  SAGRIPLWGG  VLITiVDTFF  FLFLDNYGLR  KLEAFFGlLi>
              Nramp1      IGTAIsFnLL  SAGRIPLWGG  VLITiVDTFF  FLFLDNYGLR  KLEAFFGlLi>
              BovNramp1   IGTAIAFSLL  SAGRIPLWGG  VLITVVDTFF  FLFLDNYGLR  KLEAFFGFLi  200
                                      TM4

NRAMP1      TIMALTFGYE  YVVArPeQGA  LLrGLFLPSC  PGCGhPELLQ  AVGIvGAIIM>
              Nramp1      TIMALTFGYE  YVVAhPsQGA  LLkGLvLPtC  PGCGQPELLQ  AVGIvGAIIM>
              BovNramp1   TIMALTFGYE  YVVAQPAQGA  LLQGLFLPSC  PGCGQPELLQ  AVGIIGAIIM  250
                          TM5
```

FIG. 2A

```
NRAMP1    PHNIYLHSaL VKSREiDRaR RADIREANMY FLIEATIALS VSFiINLFVM>
Nramp1    PHNIYLHSaL VKSREVDRtR RvDvREANMY FLIEATIALS VSFiINLFVM>
BovNramp1 PHNIYLHSSL VKSREVDRSR RADIREANMY FLIEATIALS VSFLINLFVM 300
                                                       ──────────
                                                          TM7

NRAMP1    AVFGQAFYqk TNQAAFNICA nSSLHDYAkI FPmNNaTVAV DIYQGGVILG>
Nramp1    AVFGQAFYqQ TNeeAFNICA nSSLqmYAkI FPRdNnTVsV DIYQGGVILG>
BovNramp1 AVFGQAFYKQ TNQAAFNICA DSSLHDYAPI FPRNNLTVAV DIYQGGVILG 350
          ──────────
             TM6

NRAMP1    CLFGPaALYI WAiGLLAAGQ SSTMTGTYAG QFVMEGFLrL RWSRFARVLL>
Nramp1    CLFGPaALYI WAVGLLAAGQ SSTMTGTYAG QFVMEGFLKL RWSRFARVLL>
BovNramp1 CLFGPPALYI WAVGLLAAGQ SSTMTGTYAG QFVMEGFLKL RWSRFARVLL 400
          ──────────            ·········· Transport motif
                TM8

NRAMP1    TRSCAILPTV LvAVFRDLRD LSGLNDLLNV LQSLLLPFAV LPILTFTSMP>
Nramp1    TRSCAILPTV LvAVFRDLkD LSGLNDLLNV LQSLLLPFAV LPILTFTSMP>
BovNramp1 TRSCAILPTV LLAVFRDLRD LSGLNDLLNV LQSLLLPFAV LPILTFTSMP 450
          ──────────
             TM9

NRAMP1    tLMQEFANGL lnKVvTSSIM VLVCAiNLYF VvSYLPSLPH PAYFgLaALL>
Nramp1    AvMQEFANGr mSKaITScIM aLVCAiNLYF VISYLPSLPH PAYFgLvALf>
BovNramp1 ALMQEFANGL VSKVITSSIM VLVCAVNLYF VISYLPSLPH PAYFSLVALL 500
                                ──────────
                                   TM11

NRAMP1    AAAYLGLsTY LVWTCclahG ATpLAHSSHh hFLYGLiEED Q-KGeTSG>
Nramp1    AigYLGLTaY LaWTCciahG ATfLtHSSHk hFLYGLPnEe QggvqgSG>
BovNramp1 AAAYLGLTTY LVWTCLITQG ATLLAHSSHQ RFLYGLPEED QEKGRTSG  548
          ──────────
             TM12
```

FIG. 2B

Association of bovine *NRAMP1* SSCA polymorphism with bovine resistant and susceptible phenotypes in unrelated individuals

|  | Resistant Phenotype | Susceptible Phenotype |
|---|---|---|
| Resistant Alleles (SSCPr) | 9* | 2 |
| Susceptible Alleles (SSCPs) | 2 | 9 |
| Number of Cattle | 11 | 11 |

*Significant Association - $p = 0.0089$ (Fisher's Exact Analysis), RR = 4.5±1.69% (99% CI).

FIG. 3B

```
SEQ ID NO. 10    gcttgccatgcccgtgagggctgcccggcacgccagccactcgcacagagagtgcccgagcctgcggtcctcATGTCAGGTGACA    86
SEQ ID NO.  9                                                                 *  M  S  G  D     4

CGGGCCCCCAAAGCAGGAGGAGGACCAGATATGGCTCCATCTCCAGCCCCAGTCCAGAGCCACAGCCAAGCACCTCCCGGAGGG    172
                 T  G  P  P  K  Q  G  G  T  R  Y  G  S  I  S  S  P  P  S  P  P  Q  Q  A  P  P  G  G     33

ACCTACTAAGTGAGAAGATCCCCATTCCGGATACAGAATCGGGTACATTCAGCTGAGGAAGCTGTGGGCCTTCACGGGGCCTGG    258
                 T  Y  L  S  E  K  I  P  I  P  D  T  E  S  G  T  F  S  L  R  K  L  W  A  F  T  G  P  G     62

ATTCCTCATGAGCATCGCATTCCTGGACCCAGGAAACATTGAGTCGGATCTTCAGGTGGGCTGTGGGATCTCAAACTGCTCT    344
                 F  L  M  S  I  A  F  L  D  P  G  N  I  E  S  D  L  Q  A  G  A  V  A  G  F  K  L  L     90

GGGTGCTGCTGTGGGCCACAGTGTTGGGCTTGCAGCCCGGACTGTGGCTGCCCGGCTGGGACAGGCAAGGACTTGGGC    430
                 W  V  L  L  W  A  T  V  L  G  L  L  C  Q  R  L  A  A  R  L  G  V  V  T  G  K  D  L  G    119

GAGGTCTGCCATCTCTACTACCCTAAGGTGCCCCGCATTCTCCTCTGGCTGACCATCGAGCTGGCTAGCCATGTGGGCTCAGACATGCA    516
                 E  V  C  H  L  Y  Y  P  K  V  P  R  I  L  L  W  L  T  I  E  L  A  I  V  G  S  D  M  Q    148

GGAAGTCATTGGCACAGCTATTGCATTCAGTCTGCTCTCCGCCGAGAATCCCACTCTGGGGTGTGTCATCACCGTCGTGG    602
                 E  V  I  G  T  A  I  A  F  S  L  L  S  A  G  R  I  P  L  W  G  G  V  L  I  T  V  V    176

ACACTTTCTTCCTCTTCCTCGATAACTACGGGTTGCGAAGCTGGAAGCTCTTTTTTGGATTTCTTATTACCATAATGGCCTTG    688
                 D  T  F  F  L  F  L  D  N  Y  G  L  R  K  L  E  A  F  F  G  F  L  I  T  I  M  A  L    205

ACCTTCGGCTATGAGTACGTGGTTGCAGCCCGTGCTCAGCCGTTCCAGGCATTGCTGCAGGGCCTGTTCCTGCCCAGGCTGTGG    774
                 T  F  G  Y  E  Y  V  V  A  Q  P  A  Q  G  A  L  L  Q  G  L  F  L  P  S  C  P  G  C  G    234

CCAGCCCGAGCTGCTGCAAGCTGCTGGGCCATCATTGGGCGACATCATCGGGGCGATACTCCGAGAGGCCAACATGTACTTCCTGATTGAAGCCACCATCGCCCTGTCTGTC    860
                 Q  P  E  L  L  Q  A  V  G  I  I  G  A  I  I  M  P  H  N  I  Y  L  H  S  S  L  V  K    262

CTCGAGAGGTAGACCGGTCCCGGCGGGCGGCGACATCCGAGAGGCCAACATGTACTTCCTGATTGAAGCCACCATCGCCCTGTCTGTC    946
                 S  R  E  V  D  R  S  R  R  A  D  I  R  E  A  N  M  Y  F  L  I  E  A  T  I  A  L  S  V    291

TCCTTCCTCATCAACCTGTTTGTCATGGCTGTCTTTGGGCAAGCCTTCTACAAGCAAACCAACCAGGCTGCCTTCAACATCTGTGC    1032
                 S  F  L  I  N  L  F  V  M  A  V  F  G  Q  A  F  Y  K  Q  T  N  Q  A  A  F  N  I  C  A    320
```

FIG. 4A

```
CGACAGCAGCCTCCACGACTACGCGCCGATCTTCCCAGGAACAACCTGACCGTGGCAGTGGACATTTACCAAGGAGGCGTGATCC  1118
 D  S  S  L  H  D  Y  A  P  I  F  P  R  N  N  L  T  V  A  V  D  I  Y  Q  G  G  V  I      348
TGGGCTGCCTCTTTGGTCCTCCAGCCCTGTACATCTGGGCCGTGGGTCTCCTGGCTGCAGAGCTCCACCATGACCGGCACC         1204
 L  G  C  L  F  G  P  P  A  L  Y  I  W  A  V  G  L  L  A  A  G..Q..S..T..M..T..G..T..     377
TACGCGGGACAGTTTGTGATGGAGGGCTTCCTGAAGCTGCGGTGGTCACGCTTCGCCCGAGTCCTGCTCACTCGCTCCTGCGCCAT    1290
 Y..A..G..Q..F..V..M..E..G..F..L..K..L..R..W..S..R..F..A..R  V  L  L  T  R  S  C  A  I    406
CCTGCCCACTGTCCTGCTCGCTGTCTTCAGGGACCTGCGTGACCTCAGTGGCCTCAATGACCTCAATGTGCAGAGCCTGC         1376
 L  P  T  V  L  L  A  V  F  R  D  L  R  D  L  S  G  L  N  D  L  L  N  V  L  Q  S  L      434
TGCTTCCCTTGCCTGTGCTCCCATCCTCACCTTCACCAGCATGCCCGCCCTGATGCAGGAGTTTGCCAATGGCCTGGTGAGCAAA    1462
 L  L  P  L  P  V  L  P  I  L  T  F  T  S  M  P  A  L  M  Q  E  F  A  N  G  L  V  S  K   463
GTTATCACTTCCTCCATCATGGTCCTGGTGTGCGCCGTCAACCTTTACTTCGTGATCAGCTACTTGCCCAGCCTGCCCCACCCTGC   1548
 V  I  T  S  S  I  M  V  L  V  C  A  V  N  L  Y  F  V  I  S  Y  L  P  S  L  P  H  P  A   492
CTACTTCAGCCTTGTAGCACTGCTGGCCGCAGCCTACCTGGGCCTCACCACTTACCTGGTCTGTCTCATCACCCAGGGAG         1634
 Y  F  S  L  V  A  L  L  A  A  A  Y  L  G  L  T  T  Y  L  V  W  T  C  L  I  T  Q  G      520
CCACTCTTGCTGGCCACCAGTTCCCACCAACGCTTCCTGTATGGGCTTCCTGAAGAGGATCAGGAGAAGGGGAGGACCTCGGGATGA  1720
 A  T  L  L  A  H  S  S  H  Q  R  F  L  Y  G  L  P  E  E  D  Q  E  K  G  R  T  S  G  *   548
gctccaccaggcctgctgaaggcagcagacaagggtgaatgagtgggcacagtggcctgtcagacaaggtgtgtgtgtgtgtat     1806
gtgtgtgaaggcagcagacaagcagacaggagagtctgcgaagctgccaacgtgagttccagagggagctgtgtgtgtgacactg    1892
gcctgccagacgacaaggggtgtgtgtgtgcctgtgtgtgcatgcacagcaagacggagaggagttctgaaggcagcagcaacg     1978
tgagttccataggacctgctatttcctagctcagatctcagtgttcttgactataaatgggacaccttaaaatcataattcatcaa   2064
aatagacacttgaacgcagagcctagcacttcagatttaaaaacaaaaagtactgagcactatcaca                       2150
ggagtgacctgacagacagaccaccccactgctaggtggaccaggctcccaaactgattaaaataagagtctgaaatgctaataaa    2236
tgctgttgtgcttagtccccgagaaaaaaaaaa  2269
```

FIG. 4B

Sequence Differences in Naturally Susceptible (S) and Resistant (R) Bovine at the 3' Untranslated region of Bovine NRAMP1

| Phenotype | Nucleotides (starting at position 1779) | SEQ ID NO. |
|---|---|---|
| R | GGGTGTGTGTGTGTGTGTGTGTGTATGTGTGT GAAGGCAGCAAGACAGACAGGGAGTTCTGGAAGC TGGCCAACGTGAGTTCCAGAGGGACCTGTGTGTG TGTGACACACTGGCCTGCCAGACAAGGGTGTGTG TGTGTGTGTGTGTGTGT | SEQ ID NO. 11 |
| S | GGGGGTGTGTGTGTGTGTGTATGTGTGTGAAGGC AGCAAGACAGACAGGGAGTTCTGGAAGCTGGCCA ACGTGAGTTCCAGAGGGACCTGTGTGTGTGTGAC ACACTGGCCTGCCAGACAAGGGTGTGTGTGTGTG TGTGTGTGTGTGTGTGT | SEQ ID NO. 12 |
| S | GGGGGTGTGTGTGTGTGTGTATGTGTGTGAAG GCAGCAAGACAGACAGGGAGTTCTGGAAGCTGGC CAACGTGAGTTCCAGAGGGACCTGTGTGTGTGTG ACACACTGGCCTGCCAGACAAGGGTGTGTGTGTG TGTGTGTGTGTGTGTGT | SEQ ID NO. 13 |
| S | GGGGGTGTGTGTGTGTGTGTGTATGTGTGTGA AGGCAGCAAGACAGACAGGGAGTTCTGGAAGCTG GCCAACGTGAGTTCCAGAGGGACCTGTGTGTGTG TGACACACTGGCCTGCCAGACAAGGGTGTGTGTG TGTGTGTGTGTGTGTGT | SEQ ID NO. 14 |

FIG. 7A

Generalized Sequence of Bovine NRAMP1 at the 3' Untranslated region associated with resistance:

SEQ ID NO.: 15   GGGTGT(GT)$_{10}$AT(GT)$_3$(N)$_{61}$(GT)$_5$(N)$_{24}$(GT)$_{13}$

FIG. 7B

Generalized Sequence of Bovine NRAMP1 at the 3' Untranslated region associated with susceptiblity:

GGGGGT(GT)$_{<10}$AT(GT)$_3$(N)$_{<61}$(GT)$_5$(N)$_{<24}$(GT)$_{>13}$

FIG. 7C

|  | 10 | 20 | 30 | 40 | 50 | 60 |
|---|---|---|---|---|---|---|
| Bos spp. | .TCCCACCAA | CGCTTCCTGT | ATGGGCTTCC | TGAAGAGGAT | CA.GGAGAAG | GGGAGGACCT |
| Bison bison | .TCCCACCAA | CGCTTCCTGT | ATGGGCTTCC | TGAAGAGGAT | CA.GGAGAAG | GGGAGGACCT |
| Odocoileus virginianus | .TCCCACCAA | CGCTTCCTGT | ATGGGCTTCC | TGGAGAGGAT | CA.GGAGAAG | GGGAGGACCT |
| Capra hirus | ...CACCAA | CGCTTCCTGT | ATGGGCTTCC | TGAAGAGGAT | CA.GGAGAAG | GGGAGGACCT |
| Alces alces | .TCCCACCAA | CGCTTCCTGT | ATGGGCTTCC | TGAAGAGGAT | CA.GGAGAAG | GGGAGGACCT |
| Cervus canadensis | .TCCCACCAA | CGCTTCCTGT | ATGGGCTTCC | TGAAGAGGAT | CAGGGAGAAT | GGGAGGACCT |
| Cervus elaphus | .TCCCACCAA | CGCTTCCTGT | ATGGGCTTCC | TGAAGAGGAT | CA.GGAGAAT | GGGAGGACCT |
| Dama dama | .TCCCACCAA | CGCTTCCTGT | ATGGGCTTCC | TGAAGAGGAT | CA.GGAGAAT | GGGAGGACCT |
| Elaphurus davidianus | .TCCCACCAA | CGCTTCCTGT | ATGGGCTTCC | TGAAGAGGAT | CA.GGAGAAT | GGGAGGACCT |
| Ursus spp. | .TCCCACCAA | CGCTTCCTGT | ATGGGCTTCC | TGAAGAGGAT | CA.GGAGAAG | GGGAGGACCT |
| Sus scrofa | .TCCCACCAA | CGCTTCCTGT | ATGGGCTTCC | TGAAGAGGAT | CA.GGAGAAG | GGGAGGACCT |
| Oreamnos americanus | .TCCCACCAA | CGCTTCCTGT | ATGGGCTTCC | TGGAGAGGAT | CA.GGAGAAG | GGGAGGACCT |

|  | 70 | 80 | 90 | 100 | 110 | 120 |
|---|---|---|---|---|---|---|
| Bos spp. | CGGGATGAGC | TCCCACCAGG | GCCTGGCCAC | GGGTGGAATG | AGTGGGCACA | GTGGCCTGTC |
| Bison bison | CGGGATGAGC | TCCCACCAGG | GCCTGGCCAC | GGGTGGAATG | AGTGGGCACA | GTGGCCTGTC |
| Odocoileus virginianus | CGGGATGAGC | TCCCACCAGG | GCCTGGCCAC | AGTGGGATG | AGTGGGCACA | GTGGCCTGTC |
| Capra hirus | CGGGATGAAC | TCCCACCAGG | GCCTGGCCAC | GGGTGGGATG | AGTGACCACA | GTGGCCTGTC |
| Alces alces | CAGGATGAGC | TCCCACCAGG | GCCTGGCCAC | GGGTGGAATG | AGTGGGCACA | GTGGCCTGCC |
| Cervus canadensis | CAGGATGAGC | TCCCACCAGG | ACCCGGCCAC | GGGTGGGATG | AGTGGGCACA | GTGGCCTGCC |
| Cervus elaphus | CGGGATGAGC | TCCCACCAGG | ACCCGGCCAC | GGGTGGGATG | AGTGGGCACA | GTGGCCTGCC |
| Dama dama | CGGGATGAGC | TCCCACCAGG | ACCCGGCCAC | GGGTGGGATG | AGTGGGCACA | GTGGCCTGCC |
| Elaphurus davidianus | CAGGATGAGC | TCCCACCAGG | GCCCGGCCAC | GGGTGGGATG | AGTGGGCACA | GTGGCCTGCC |
| Ursus spp. | CAGGATGAGC | TCCCACCAGG | GCCTGGCCAC | GGGTGGGATG | AGTGGGCACA | GTGGCCTGCC |
| Sus scrofa | CGGGATGAGC | TCCCACCAGG | GCCTGGCCAC | AGTGGGATG | AGTGGGCACA | GTGGCTTGCC |
| Oreamnos americanus | CGGGATGAAC | TCCCACCAGG | GCCCGGCCAC | GGGTGGGATG | AGTGACCACA | GTGGCCTGCC |

FIG. 8A-1

|  | 130 | 140 | 150 | 160 | 170 | 180 |
|---|---|---|---|---|---|---|
| Bos spp. | AGACAAGGGT | GTGTGTGTGT | GTGTGTGTGT | GTATGTGTGT | GAAGGCAGCA | AGACAGACAG |
| Bison bison | AGACAAGGGT | GTGTGTGTGT | GTGTGTGTGT | GTATGTGTGT | GAAGGCAGCA | AGACAGACAG |
| Odocoileus virginianus | AGACAAAG.. | GGGTGTGTGT | GTGTGTGTGT | GTATGTGTGC | GAAGGCAGCA | AGACAGACAG |
| Capra hirus | AGACAAGG.. | ....GTGTGT | GTGTGTGTGT | GTGTGTGTG. | .......... | .......... |
| Alces alces | AGACAAGGGT | GTGTGTGTGT | GTGTGTGTGT | ATGTGTGTGT | .......... | .......... |
| Cervus canadensis | AGACAAGGGT | GTGTGTGTGT | GTGTGTGTGT | GTGTGTGTG. | .......... | .......... |
| Cervus elaphus | AGACAAGGGT | GTGTGTGTGT | GTGTGTGTGT | GTGTGTGTG. | .......... | .......... |
| Dama dama | AGACAAGG.. | GTGTGTGTGT | GTGTGTGTGT | GTGTGTGTG. | .......... | .......... |
| Elaphurus davidianus | AGACAAGGGG | GTGTGTGTGT | GTGTGT.... | .......... | .......... | .......... |
| Ursus spp. | AGACAAGGGT | GTGTGTGT.. | .......... | .......... | .......... | .......... |
| Sus scrofa | AGACAAGGGT | GTGTGTGT.. | .......... | .......... | .......... | .......... |
| Oreamnos americanus | AGACAAGGGT | GTGTGTGTGT | GTGTGTGTGT | GTGTCTGTG. | .......... | .......... |

|  | 190 | 200 | 210 | 220 | 230 | 240 |
|---|---|---|---|---|---|---|
| Bos spp. | GGAGTTCTGG | AAGCTGGCCA | ACGTGAGTTC | CAGAGGGACC | TGTGTGTGTG | TGACACACTG |
| Bison bison | GGAGTTCTGG | AAGCTGGCCA | ACGTGAGTTC | CAGAGGGACC | TGTGTGTGTG | TGACACACTG |
| Odocoileus virginianus | GGAGTTCTGG | AAGCTGGCCA | ACGTGAGTTC | CAGAGGGACC | TGTGTGTGTG | TGACACACTG |
| Capra hirus | ........TGT | GTGTGCATGC | ACAGCAAGAT | GGAGAGGGAG | TTCACGGGTG | GGATGAGTGG |
| Alces alces | ........TGT | GTGTGTGC.. | .......... | .......... | .......... | .......... |
| Cervus canadensis | ........TGC | GCGCGCGCGC | GC........ | .......... | .......... | .......... |
| Cervus elaphus | ........TGT | GTGCGGCGCGC | GC........ | .......... | .......... | .......... |
| Dama dama | ........TGT | GTGCGCCGCGC | GC........ | .......... | .......... | .......... |
| Elaphurus davidianus | .......... | .GCAC..... | .......... | .......... | .......... | .......... |
| Ursus spp. | .......... | .......... | .......... | .......... | .......... | .......... |
| Sus scrofa | .......... | .......... | .......... | .......... | .......... | .......... |
| Oreamnos americanus | ........TGT | GTGCGCCGCGC | A......... | .......... | .......... | .......... |

|  | 250 | 260 | 270 | 280 | 290 | 300 |
|---|---|---|---|---|---|---|
| Bos spp. | GCCTGCCAGA | CAAGGGTGTG | TGTGTGTGTG | TGTGTGTGTG | TGCATGCACA | GCAAGACGGA |
| Bison bison | GCCTGCCAGA | CAAGGGTGTG | TGTGTGTGTG | TGTGTGTGTG | TGCATGCACA | GCAAGACGGA |
| Odocoileus virginianus | GCCTGCCAGA | CAAAG..GTG | TGTGTGTGTG | TGTGTGTGTG | TGCATGCACA | GCAAGACGGA |
| Capra hirus | GCACAGTGGC | CTGCCAGACA | AGG....GTG | TGTGTGTGTG | TGCACGCACA | GCAAGATGGA |
| Alces alces | .......... | .......... | .......... | ......GCG | CTCACCCACA | ACAAGACGGA |
| Cervus canadensis | .......... | .......... | .......... | ....GAGCG | CTCACACACA | GCAAGACAGA |
| Cervus elaphus | .......... | .......... | .......... | ......GCG | CTCACACACA | GCAAGACAGA |
| Dama dama | .......... | .......... | .......... | ......GCG | CTCACACACA | GCAAGACAGA |
| Elaphurus davidianus | .......... | .......... | .......... | ....GCGCG | CTCACACACA | GCAAGACAGA |
| Ursus spp. | .......... | .......... | .......... | ........G | GTCACCCACA | GCAAGACGGA |
| Sus scrofa | .......... | .......... | .......... | ........G | GTCACCCACA | GCAAGACGGA |
| Oreamnos americanus | .......... | .......... | .......... | .......... | ......CACA | GCAAGATGGA |

|  | 310 | 320 | 330 | 340 | 350 | 360 |
|---|---|---|---|---|---|---|
| Bos spp. | GAGGGAGTTC | TGGAAGGCAG | CCAACGTGAG | TTCCATAGGG | ACCTGCTATT | TCCTAGCTCA |
| Bison bison | GAGGGAGTTC | TGGAAGGCAG | CCAACGTGAG | TTCCATAGGG | ACCTGCTATT | TCCTAGCTCA |
| Odocoileus virginianus | GAGGGAGTTC | TGGAAGGCAG | CCAACGTGAG | TTCCATAGGG | ACCTGCTATT | TCCTAGCTCA |
| Capra hirus | CAGGGAATTT | TGGAAGCCGG | CCAA...... | .GCCATAGGG | ACCTGCTATT | TCCTAGCTCA |
| Alces alces | GAGGGAGTTC | TGGAAGCCGG | ACAACGTGAG | TTCCATAGGG | ACCTGCTGTT | TCCTAGCTCA |
| Cervus canadensis | GAGGGAGTTC | TGGAAGCCGG | ACGACGTGAG | TTCCATAGGG | ACCTGCTGTT | TCCTAGCTCA |
| Cervus elaphus | GAGGGAGTTC | TGGAAGCAGG | ACGACGTGAG | TTCCATAGGG | ACCTGCTGTT | TCCTAGCTCA |
| Dama dama | GAGGGAGTTC | CGGAAGCCGG | ACGACGTGAG | TTCCATAGGG | ACCTGCTGTT | TCCTAGCTCA |
| Elaphurus davidianus | GAGGGAGTTC | TGGAAGCAGG | ACGACGTGAG | TTCCATAGGG | ACCTGCTGTT | TCCTAGCTCA |
| Ursus spp. | GAGGGAGTTC | TGGAAGCCGG | ACAACGTGAG | TTCCATAGGG | ACCTGCTGTT | TCCTAGCTCA |
| Sus scrofa | GAGGGAGTTC | TGGAAGCCGG | ACAACGTGAG | TTCCATAGGG | ACCTGCTGTT | TCCTAGCTCA |
| Oreamnos americanus | GAGGGAATTC | TGGAAGCCGG | CCAA...... | .GCCATAGGA | GCCTGCTATT | TCCTAGCTCA |

|                        | 370        | 380        | 390        | 400        | 410        | 420        |
|------------------------|------------|------------|------------|------------|------------|------------|
| Bos spp.               | GATCTCAGTG | TTCTTGACTA | TAAAATGGGG | ACACCTACCT | TGGAGTGGTT | GTAAATAAGA |
| Bison bison            | GATCTCAGTG | TTCTTGACTA | TAAAATGGGG | ACACCTACCT | TGGAGTGGTT | GTAAATAAGA |
| Odocoileus virginianus | GATCTCAGTG | TTCTTGACTA | TAAAATGGGG | ACACCCACCT | TGGAGTGGTT | GTTAATAAGA |
| Capra hirus            | GATCTCGGTA | TTCTTGAGTA | TTAAATGGGG | ACACCTACCT | TGCAATGGTT | GTAAATAAGA |
| Alces alces            | GATCTCAGTG | TTCTTGATTA | TAAAATGGGG | ACACCTACCT | TGCAACGGTT | GTAAATAAGA |
| Cervus canadensis      | TTCTTCACTA | TAAAATGGGG | ACACCTACCT | TGCAATGGTT | GTAAATAAGA |            |
| Cervus elaphus         | GATCTCAGTG | TTCTTCACTA | TAAAATGGGG | ACACCTACCT | TGCAATGGTT | GTAAATAAGA |
| Dama dama              | GATCTCAGTG | TTCTTCACTA | TAAAATGGGG | ACACCTACCT | TGCAATGGTT | GTAAATAAGA |
| Elaphurus davidianus   | GATCTCAGTG | TTCTTGACTA | TAAAATGGGG | ACACCTACCT | TGCAATGGTT | GTAAATAAGA |
| Ursus spp.             | GATCTCAGTG | TTCTTGACTA | TAAAATGGGG | ACACCTACCT | TGCAATGGTT | GTAAATAAGA |
| Sus scrofa             | GATCTCAGTG | TTCTTGACTA | TAAAATGGGG | ACACCTACCT | TGCAATGGTT | GTAAATAAGA |
| Oreamnos americanus    | GATCTTGGTA | TTCTTGAGTA | TTAACTGGGG | ACACCTACCT | TGCAATGGTT | GTAAATAAGA |

|                        | 430        | 440        | 450        |              |
|------------------------|------------|------------|------------|--------------|
| Bos spp.               | CAC..TTGAA | CGCAGAGCCT | AGCACTTCAG | ATT SEQ ID NO. 16 |
| Bison bison            | CAC..TTGAA | CGCAGAGCCT | AGCACTTCAG | ATT SEQ ID NO. 17 |
| Odocoileus virginianus | CAC..TTGAA | CGCAGAACCT | AGCACCTCAG | ATT SEQ ID NO. 18 |
| Capra hirus            | CAC..TTGAA | CGCAGAGCCT | AGCACTTCAG | ATT SEQ ID NO. 19 |
| Alces alces            | CACATTGGAA | CGCAGAGGCT | AGCACTTCAG | ATT SEQ ID NO. 20 |
| Cervus canadensis      | CAC..TTGAA | TGCAGAGCCT | AGCACTTCAG | ATT SEQ ID NO. 21 |
| Cervus elaphus         | CAC..TTGAA | TGCAGAGCCT | AGCACTTCAG | ATT SEQ ID NO. 22 |
| Dama dama              | CAC..TTGAA | CGCAGAGCCT | AGCACTTCAG | ATT SEQ ID NO. 23 |
| Elaphurus davidianus   | CAC..TTGAA | TGCAGAGCCT | AGCACTTCAG | ATT SEQ ID NO. 24 |
| Ursus spp.             | CAC..TAGAA | CGCAGAGCCT | AGCACTTCAG | ATT SEQ ID NO. 25 |
| Sus scrofa             | CAC..TTGAA | CGCAGAGCCT | AGCACTTCAG | ATT SEQ ID NO. 26 |
| Oreamnos americanus    | CAC..TTGAA | CGCAGAGCCT | AGCACTTCAG | ATT SEQ ID NO. 27 |

FIG. 8A-4

|  |  |  |  |  |  |  |
|---|---|---|---|---|---|---|
| | | | | pts | | |
| BovNramp1 | MSGDTGPPKQ | GGTRYGSISS | PPSPEPQQAP | PGGTYLSEKI | PIPDTESGTF | 50 |
| BisNramp1 | MSGDTGPPKQ | GGTRYGSISS | PPSPEPQQAP | PGGTYLSEKI | PIPDTESGTF | |
| | | | | &&&&&& | | |
| | | | | PKC | | |
| BovNramp1 | SLRKLWAFTG | PGFLMSIAFL | DPGNIESDLQ | AGAVAGFKLL | WVLLWATVLG | 100 |
| BisNramp1 | SLRKLWAFTG | PGFLMSIAFL | DPGNIESDLQ | AGAVAGFKLL | WVLLWATVLG | |
| | PKC | TM1 | | | TM2 | |
| BovNramp1 | LLCQRLAARL | GVVTGKDLGE | VCHLYYPKVP | RILLWLTIEL | AIVGSDMQEV | 150 |
| BisNramp1 | LLCQRLAARL | GVVTGKDLGE | VCHLYYPKVP | RILLWLTIEL | AIVGSDMQEV | |
| | | | | | TM3 | |
| BovNramp1 | IGTAIAFSLL | SAGRIPLWGG | VLITVVDTFF | FLFLDNYGLR | KLEAFFGFLI | 200 |
| BisNramp1 | IGTAIAFSLL | SAGRIPLWGG | VLITIVDaEF | FLFLDNYGLR | KLEAFFGFLI | |
| | | TM4 | | | | |
| BovNramp1 | TIMALTFGYE | YVVAQPAQGA | LLQGLFLPSC | PGCGQPELLQ | AVGIIGAIIM | 250 |
| BisNramp1 | TIMALTFGYE | YVVAQPAQGA | LLQGLFLPSC | PGCGQPELLQ | AVGIIGAIIM | |
| | TM5 | | | | | |

SEQ ID NO. 9 BovNramp1
SEQ ID NO. 28 BisNramp1

FIG. 8B-1

```
BovNramp1  PHNIYLHSSL VKSREVDRSR RADIREANMY FLIEATIALS VSFLINLFVM 300
BisNramp1  PHNIYLHSSL VKSREVDRSR RADIREANMY FLIEATIALS VSFLINLFVM
                                                      ━━━━━━━━━━
                                                         TM7

BovNramp1  AVFGQAFYKQ TNQAAFNICA DSSLHDYAPI FPRNNLTVAV DIYQGGVILG 350
BisNramp1  AVFGQAFYKQ TNQAAFNICA nSSLqDYAPI FPRNNLTVAV DIYQGGVILG
                                                      ━━━━━━━━━━
                                                         GGG BovNramp1  CLFGPPALYI WAVGLLAAGQ SSTMTGTYAG QFVMEGFLKL RWSRFARVLL 400
BisNramp1  CLFGPaALYI WAVGLLAAGQ SSTMTGTYAG QFVMEGFLKL RWSRFARVLL
           ━━━━━━━━━━━━━━━━━━━━ ··········         Transport motif
                  TM8

BovNramp1  TRSCAILPTV LLAVFRDLRD LSGLNDLLNV LQSLLLPFAV LPILTFTSMP 450
BisNramp1  TRSCAILPTV LLAVFRDLRD LSGLNDLLNV LQSLLLPFAV LPILTFTSMP
           ━━━━━━━━━━━━━━━━━━━━                      ━━━━━━━━━━
                  TM9                                   TM10

BovNramp1  ALMQEFANGL VSKVITSSIM VLVCAVNLYF VISYLPSLPH PAYFSLVALL 500
BisNramp1  ALMrEFANGL VSKVITSSIM VLVCAVNLYF VISYvPSLPH PAYFSLVALL
                      ━━━━━━━━━━━━━━━━━━━━
                            TM11

BovNramp1  AAAYLGLTTY LVWTCLITQG ATLLAHSSHQ RFLYGLPEED QEKGRTSG    548
BisNramp1  AAAYLGLTTY LVWTCLITQG ATLLAHSSHQ RFLYGLPEED QEKGRTSG
           ━━━━━━━━━━
              TM12
```

FIG. 8B-2

Examples of the Length and Pattern of Microsatellites for Several Species
of Mammals Using Bovine Nramp1 3' end Primer Pair
F1655/3 - end2 for Amplification

| Species of Mammals | Length (base pairs) | Number of Microsatellites | Patterns |
|---|---|---|---|
| Cattle | 448bp | 3 | (GT)12..(GT)5..(GT)14 |
| American Bison | 448bp | 3 | (GT)12..(GT)5..(GT)14 |
| White-tailed Deer | 446bp | 3 | (GT)9..(GT)6..(GT)12 |
| Red Deer | 347bp | 2 | (GT)18(GC)7 |
| Fallow Deer | 345bp | 2 | (GT)17(GC)7 |
| Elk | 349bp | 2 | (GT)16(GC)7 |
| Pere David's Deer | 327bp | 1 | (GT)9..(CG)4 |
| Moose | 345bp | 1 | (GT)14TA(GT)5 |
| Goat | 402bp | 2 | (GT)7..(GT)16 |
| Mountain Goat | 329bp | 1 | (GT)12CT(GT)4 |
| Dall Sheep | 416bp | 2 | (GT)19..(GT)9 |
| Caribou | 309bp | 1 | (GT)5 |
| Reindeer | 309bp | 1 | (GT)5 |
| Pig | 309bp | 1 | (GT)5 |
| Barasinga Cervus | 309bp | 1 | (GT)5 |
| Samber Cervus | 309bp | 1 | (GT)5 |
| Black Bear | 309bp | 1 | (GT)5 |
| Grizzly Bear | 309bp | 1 | (GT)5 |
| Polar Bear | 309bp | 1 | (GT)5 |
| Red Mazama | 307bp | 1 | (GT)5 |
| Elephant | 309bp | 1 | (GT)5 |

FIG. 8C

3' Untranslated Sequence of Bison NRAMP1 in Resistant Bison

SEQ ID NO 29

```
                                     Fmicro
     1676-GGGCTTCCTGAAGAGGATCAGGAGAAGGGGAGGACCTCG          1714
            G  L  P  E  E  D  Q  E  K  G  R  T  S
GGGATGagctcccaccagggcctggccacgggtgggatgagtgggcacag        1763
 G  @
tggcctgtcagacaagggtgtgtgtgtgtgtgtgtgtgtgaa                1809
                            (TG)13
Bmicro1'
ggcagcaagacagagacggagttctggaagctggccaacgtgagttccag        1859 agggacctgtgtgtgtgtgtgacacactggcctgccagacaaggg             1906
             (TG)8
tgtgtgtgtgtgtgtgtgtgtgtgtgcatgcacagcaag                   1951
(TG)16
acagagagggagttctggaagccagccaacgtgagttccatagggacctg        2001
ctatttcctagctcagatctcagtgttcttgactataaaatggggacacc        2051
taccttggaatggttgtaaataagacacttgaacgcagagcctagcactt        2101
cagatttaaaaacaaaagaatcataattccaaaagttactgagcactatc        2151
acaggagtgacctgacagacccacccagtccagggtgggacccaggctcc        2201
aaactgatttaaaataagagtctgaaaatgctaaataaatgctgttgtc         2251
ttagtccccg         2261
```

3' Untranslated Sequence of Bison NRAMP1 in Susceptible Bison

SEQ ID NO. 30

```
                                     Fmicro
     1676-GGGCTTCCTGAAGAGGATCAGGAGAAGGGGAGGACCTCG          1714
            G  L  P  E  E  D  Q  E  K  G  R  T  S
GGGATGagctcccaccagggcctggccacgggtgggatgagtgggcacag        1763
 G  @
tggcctgtcagacaagggtgtgtgtgtgtgtgtgtgtgaa                  1807
                            (TG)12
Bmicro1'
ggcagcaagacagagacggagttctggaagctggccaacgtgagttccag        1857
agggacctgtgtgtgtgtgtgacacactggcctgccagacaaggg             1904
             (TG)8
tgtgtgtgtgtgtgtgtgtgtgtgtgcatgcacagcaag                   1949
(TG)16
acagagagggagttctggaagccagccaacgtgagttccatagggacctg        1999
ctatttcctagctcagatctcagtgttcttgactataaaatggggacacc        2049
taccttggaatggttgtaaataagacacttgaacgcagagcctagcactt        2099
cagatttaaaaacaaaagaatcataattccaaaagttactgagcactatc        2149
acaggagtgacctgacagacccacccagtccagggtgggacccaggctcc        2199
aaactgatttaaaataagagtctgaaaatgctaaataaatgctgttgtc         2249
ttagtccccg         2259
```

FIG. 8D

METHOD OF IDENTIFICATION OF ANIMALS RESISTANT OR SUSCEPTIBLE TO DISEASE SUCH AS RUMINANT BRUCELLOSIS, TUBERCULOSIS, PARATUBERCULOSIS AND SALMONELLOSIS

This application claims priority of U.S. Provisional Application Ser. No. 60/031,443, filed Sep. 20, 1996.

BACKGROUND OF THE INVENTION

1. Field of the Invention

The present invention relates to a method for identifying animals that are resistant or susceptible to diseases associated with intracellular parasites. More particularly, the present invention relates to the identification of a gene, called NRAMP1, associated with the susceptibility or resistance of an animal, such as an artiodactyla, to diseases such as brucellosis, tuberculosis, paratuberculosis and salmonellosis. Still more particularly, the present invention relates to the identification of specific sequences of the 3' untranslated region (3' UTR) of bovine NRAMP1 which associate with resistance or susceptibility to bovine brucellosis, tuberculosis, paratuberculosis and salmonellosis, and to the use of the general sequence patterns to identify artiodactyl animals containing those sequences in situ, allowing therefore the identification of animals predicted to be either resistant or susceptible to diseases associated with intracellular parasites.

2. General Background

Intracellular zoonotic bacterial diseases like brucellosis and tuberculosis cause significant losses in livestock industries despite widespread application of antimicrobials, vaccination, isolation and quarantine, test and slaughter, or a combination of these. The lack of success in eradicating infectious diseases of animals using these approaches indicates a need for a different strategy, such as the development of a means to identify genetic sequences associated with resistance and/or susceptibility, where such means could allow the identification of animals that are resistant or susceptible to disease. This could then allow the treatment, prophylactic or therapeutic, or elimination of susceptible animals, and the use of and/or selective breeding of resistant animals (see, for example, Templeton et al. 1988).

Diseases such as ruminant brucellosis, tuberculosis, paratuberculosis and salmonellosis cause an estimated $250,000,000 loss annually to the U.S.A. beef and dairy industry. Further, tuberculosis especially is a health threat to all ungulates including rare and endangered mammals. These are diseases for which the usual eradication programs have been long-term, expensive, and somewhat unsuccessful. For example, bovine tuberculosis was thought to be a disease of antiquity in 1970 but has re-emerged as an endemic disease in the El Paso, Tex. dairy herds. Outbreaks of bovine tuberculosis have been reported in the past 5 years in California, Idaho, Indiana, Louisiana, Missouri, Montana, Nebraska, New Mexico, New York, North Carolina, Pennsylvania, South Carolina, Texas, Wisconsin, and Virginia (Essey and Koller 1994; and Essey M. A. 1991).

Further, each of these specific diseases are zoonotic diseases which continually threaten the U.S. population. The benefit of cattle naturally resistant to these, and other diseases would be a key component of the preharvest pathogen reduction programs like the National Hazard Analysis Critical Control Point (HACCP) program proposed for farm use (Pierson, M. D. and Corlett, D. A., 1992; and Vanderzant, C., 1985). Further, it is desired that the approach used to control these diseases use natural resistance since it is environmentally compatible.

The only method currently available for the detection of artiodactyla resistant to brucellosis or tuberculosis is by a potent in vivo challenge with virulent *Brucella abortus*, *Salmonella dublin*, *Mycobacterium paratuberculosis*, or *Mycobacterium bovis* (Templeton and Adams 1996). Unfortunately, for this assay, the tested ungulates have to be euthanized in order to culture for the specific pathogen. Males challenged with *B. abortus* or *M. bovis* must be necropsied and cultured to determine if the bacterium has been cleared (resistant) or persists (susceptible). Nonpregnant females challenged with *M. bovis* must be necropsied and cultured to determine resistance or susceptibility. Although the gametes from both males and females can be stored frozen and used in a breeding-selection program to produce naturally resistant progeny with some success, this is both extremely expensive, and inefficient. The viability of frozen gametes and embryos is variable and a much lower birth rate occurs than with natural matings. Additionally, the breeding-selection program would be based on phenotypic selection (so-called mass selection) which is not as efficient as determining genotypes and selecting resistance associated with genetic sequences directly. (See, for example, Martin et al. 1994; and Dietrich et al. 1986).

The present invention solves these prior art problems by providing an efficient and reliable method for determining whether an animal, such as an artiodactyla, is susceptible or resistant to diseases such as brucellosis, tuberculosis, paratuberculosis and salmonellosis.

SUMMARY OF THE PRESENT INVENTION

In this invention, we identify homologs of murine NRAMP1 from bovine, bison, and other artiodactyla and show that particular sequences of the 3' UTR of these NRAMP1 homologs have a highly significant association with resistance or susceptibility to diseases associated with bacterial pathogens.

More specifically, this invention relates to the discovery of distinct, naturally occurring sequences of bovine NRAMP1, where the presence of a particular sequence strongly correlates (P=0.0089) with either resistance or susceptibility to, inter alia, brucellosis, tuberculosis, paratuberculosis and salmonellosis in unrelated cattle.

The genetic sequences associated with artiodactyla NRAMP1 that statistically associate with either susceptibility or resistance involve a transversion at position 1782 of the NRAMP1 complementary (c) DNA and a polymorphic DNA microsatellite sequence difference; both of which are located in the 3' UTR. The sequence associated with resistance contains a thymine at position 1782 and a polymorphic microsatellite sequence beginning at position 1785 characterized by:

SEQ ID NO. 31: 5' $(GT)_{10}AT(GT)_3(N)_{61}(GT)_5(N)_{24}(GT)_{13}3'$ where "N" symbolizes any one of the four nucleotide bases A, C, G or T. In contrast, the sequences associated with susceptibility contain a guanine at position 1782 and a polymorphic DNA microsatellite region characterized by:

SEQ ID NO: 32: 5' $(GT)_{<10}AT(GT)_3(N)_{>61}(GT)_5(N)_{<24}(GT)_{>13}3'$ where "N" again symbolizes any one of the four nucleotide bases A, C, C or T.

These sequence differences in the 3' UTR of the NRAMP1 gene can be used to detect whether animals are susceptible or resistant to disease. For example, by screening animals for the presence of sequences associated with susceptibility or resistance, one can easily and accurately predict the susceptibility or resistance of an animal to diseases such as brucellosis, tuberculosis, paratuberculosis, salmonellosis and other diseases associated with infections of macrophages.

Once identified, susceptible animals can be segregated, prophylactically or therapeutically treated, or sacrificed. Resistant animals, on the other hand, can be safely handled, used to produce food stuffs, and/or bred to produce disease resistant animals.

BRIEF DESCRIPTION OF THE DRAWINGS

For a further understanding of the nature and objects of the present invention, reference should be had to the following detailed description, taken in conjunction with the accompanying drawings, wherein:

FIG. 1A shows the sequence of PCR primers useful in the detection of bovine NRAMP1 sequences associated with susceptibility and resistance to disease (SEQ ID NO.1 and SEQ ID NO. 2);

FIG. 1B shows the sequences of primers used to clone bovine NRAMP1 (SEQ ID NO. 3, SEQ ID NO.4, SEQ ID NO. 5, and SEQ ID NO.6);

FIG. 2 shows the predicted amino acid sequence of bovine Nramp1 (SEQ ID NO. 7), and human (SEQ ID NO. 8), and murine (SEQ ID NO. 9) Nramp1 homologs and their alignment with each other;

FIG. 3B shows the tabular results of the experiment performed in FIG. 3A;

FIG. 4 shows the nucleotide sequence (SEQ ID NO. 10) and predicted amino acid sequence (SEQ ID NO. 9) of bovine NRAMP1;

FIG. 7A shows the sequences of bovine NRAMP1 associated with susceptibility and resistance to disease (SEQ ID NO. 11, 12, 13 and 14);

FIG. 7B shows the generalized sequence of bovine NRAMP1 associated with resistance (SEQ ID NO. 15);

FIG. 7C shows the generalized sequence of bovine NRAMP1 associated with susceptibility;

FIGS. 8A1 and 8A2 (SEQ ID NO.s 16–27) show the conserved amino acid sequence alignment at the 3' UTR of various ungulates;

FIG. 8B shows an alignment of the amino acid sequences encoded by NRAMP1 of bovine (BovNramp1, SEQ ID NO. 9) and bison (BisNramp1, SEQ ID NO. 28);

FIG. 8C shows the length and pattern of microsatellites for several species of mammals;

FIG. 8D shows the 3' Untranslated Sequence of Bison NRAMP1 in Resistant (SEQ ID NO. 29) and Susceptible (SEQ ID NO. 30) bison;

DETAILED DESCRIPTION OF THE PREFERRED EMBODIMENT

Figure 3A:
FIG. 3A shows the SSCP analysis of 22 unrelated cattle, phenotypically determined (by in vivo challenge and/or by an in vitro macrophage killing assay) to be either naturally resistant or susceptible to disease.

Genetic studies in mice have demonstrated that innate susceptibility to *Mycobacterium bovis* (BCG), *Leishmania donovani*, *Salmonella typhimurim* and several atypical mycobacteriae are controlled by a single gene on Mus Musculus (MMU) 1 autosome, called Bcg, Lsh, or Ity (Mock et al. 1990; Plant et al. 1982; Schurr et al. 1991; Goto et al. 1989; Skamene et al. 1984; de Chastellier et al. 1993; and Frelier et al. 1990). Bcg mediates antimicrobial activity of macrophages against intracellular parasites early during infection (Gros et al., 1983; Blackwell et al., 1991; Roach et al., 1994; Roach et al., 1991). Cattle which are naturally resistant (R) or susceptible (S) to brucellosis were identified by in vivo *Brucella abortus* challenge experiments (Harmon et al. 1985). Studies demonstrated that macrophages from resistant cattle were better able to control intracellular replication of *B. abortus* in an in vitro assay (Harmon et al. 1989; Price et al. 1990; Campbell et al. 1992). These observations were comparable to the differences in macrophage function between mice resistant and susceptible to *M. bovis*-BCG, *Salmonella typhimurium* and *L. donovani* controlled by the Bcg/Lsh/Ity gene(s) (Radzioch et al. 1991; Kramnik et al. 1994; Blackwell et al. 1994; Gros et al. 1983; Blackwell et al. 1991; Blackwell et al. 1994; Roach et al. 1991).

In mice, an approximately 30 cM segment on MMU1 (Mock et al. 1990; Skow et al. 1987; Malo et al. 1993) including Bcg was reported to be conserved on Homo sapiens autosome (HSA) 2q (Cellier et al. 1994; White et al. 1994) and Bos taurus autosome (BTA) 2 (Womack et al. 1986; Fries et al. 1993; Adkinson et al. 1988; Beever et al. 1994). Vidal and coworkers (Vidal et al. 1993) isolated a murine Bcg candidate gene, designated natural resistance associated macrophage protein (NRAMP1), that apparently encodes a polytopic integral membrane protein that has structural features similar to prokaryotic and eukaryotic transporters. Recent studies using knock-out mice have shown that NRAMP1 is the Bcg/Lsh/Ity gene. It is suggested that the murine Nramp1 protein might function in phagolysosomal membranes as a concentrator of oxidation products of nitric oxide, mediating cytocidal activity against the ingested parasites of infected macrophage (Vidal et al. 1993; Malo et al. 1994a; Cellier et al. 1994; Malo et al. 1994b).

In the present invention, a study was undertaken to determine if a bovine homolog of the murine NRAMP1 gene was expressed in bovine macrophages and involved in susceptibility of cattle to, for example, *B. Abortus*. Comparison of human, murine and bovine homologs of the bovine NRAMP1 gene product indicates a remarkable degree of homology (see, FIG. 2). The bovine NRAMP1 cDNA encodes a protein with an overall predicted amino acid sequence homology of 86.9% and 88.6% to the human NRAMP1 and murine NRAMP1 gene products, respectively. Northern blot and RT-PCR analysis indicate that similar to the human and murine gene products, bovine NRAMP1 is principally expressed in the reticuloendothelia (RE) organs and macrophages (Vidal et al. 1993; Cellier et al. 1994; Gruenheid et al. 1995). All three homologs contain 12 potential membrane-spanning helical domains and several functional sequence motifs including an N-terminal SH3-binding PNNP motif, a 20 amino acid transport motif, also known as the "binding-protein-dependent transport system inner membrane component signature" motif within the transmembrane (TM) 8–9 segment (Vidal et al., 1993; Malo et al., 1994a; Cellier et al., 1994; Malo et al., 1994b) four Protein Kinase C (PKC) phosphorylation sites; and one predicted N-linked glycosylation site (FIG. 2). Additionally, very few substitutions in the Nramp1 protein appear to be tolerated in the membrane-spanning regions.

The bovine NRAMP1 has been mapped to BTA 2 within a group of syntenic loci conserved on HSA 2q and murine chromosome 1 overlapping the Lsh/Ity/Bcg locus (Adkinson et al. 1988; Beever et al. 1994; Cellier et al. 1994; White et al. 1994). Additionally, the interleukin-8 receptor is linked to bovine NRAMP1. The data presented herein further extends the large conserved synteny of bovine, human, and murine genes on these chromosomes. Taken altogether, these findings indicate that the observed collective properties have important structural and mechanistic roles in mediating Nramp1 function.

SSCA (single stranded conformational analysis) and SSCP (single stranded conformational polymorphism) analysis are two very similar techniques commonly used to detect differences in DNA sequences. SSCP tends to be slightly more sensitive; it can be used to detect single nucleotide differences between two sequences. SSCA is often used when detecting multiple sequence differences such as those occurring in microsatellite DNA sequence regions. In the present invention, both SSCA and SSCP analysis, along with direct DNA sequencing, were used to show that different sequences of bovine NRAMP1 associate with susceptibility or resistance to infection. The significant association of the bovine NRAMP1 conformational polymorphisms (i.e. the sequence variations) associated with natural resistance or susceptibility to bovine brucellosis, inter alia, strongly suggests that, although the inventors do not wish to be bound by theory, bovine NRAMP1 is the bovine Bcg homolog or is equally important as Bcg in regulating natural resistance to the intracellular parasites. In fact, the finding that sequence variants of bovine NRAMP1 associate with resistance or susceptibility strengthens the case for the proposed role of NRAMP1 in controlling natural resistance to brucellosis, salmonellosis, and tuberculosis in all artiodactyla.

Potential mechanisms for bovine NRAMP1 control over, or association with, resistance/susceptibility have been reviewed by others, which are incorporated herein by reference (Vidal et al. 1993; Cellier et al. 1994; Blackwell et al. 1994; Ivanyi et al. 1994; Vidal et al. 1995; Blackwell et al. 1995; Nathan 1995). Given the conservation of NRAMP1 genes in at least three species, it is likely that the fundamental function of the NRAMP1 homologs against the different intracellular pathogens, such as, but not limited to, Mycobacteriae, Brucellae, Salmonellae, and Leishmania is conserved and may be related to the level of killing by macrophages. The exact mechanism may vary with different pathogens and can include: transportation and production of nitrogen oxide; production of reactive nitrogen and oxygen intermediates; respiratory bursts and the hexose monophosphate shunt; SH3 and tyrosine kinase signal transduction; upregulation of MHC Class II expression; and interleulkin-1 production.

Given the complex structure and conservation of the predicted Nramp1 protein in three species, it would not be surprising if the proposed signaling and bactericidal mechanisms are involved in macrophage antimicrobial/parasite activity. While it is possible that the regulation of Nramp1 activity may be different in the various species, with the high degree of similarity between the species, it is more likely that the fundamental function of Nramp1 is conserved against the different intracellular pathogens, i.e. Mycobacteriae, Brucellae, Salmonellae, and Leishmania. Thus, the present invention which relates to the use of the discovered genetic variation in the NRAMP1 gene in selecting and breeding domestic and free-ranging artiodactyla that are naturally resistant to these important diseases could play a key role in preharvest pathogen reduction in the National Hazard Critical Control Point (HACCP) program for farm use (Pierson, M. D. and Corlett, D. A., 1992; and Vanderzant, C., 1985).

The mechanisms by which the sequence variations in the 3' UTR of NRAMP1 contribute to susceptibility or resistance to disease caused by infection by intracellular parasites is not precisely known. However, and while not intending to be bound by or to a particular theory, applicants suggest that the variations in the 3' UTR sequence could affect the translation of the bovine NRAMP1 message, with one sequence being transcribed more or less than the other. One possible mechanism by which this could occur could be selective ribosome instability on either the resistance-associated or susceptible-associated mRNA. This instability may result in a translation complex that is more likely to fall off the message of one sequence type than the other.

An embodiment of the instant invention therefore involves the identification, cloning and use of an artiodactyla gene associated with resistance and susceptibility to disease(s) involving intracellular parasites, such as brucellosis, tuberculosis, paratuberculosis and salmonellosis. More particularly, the present invention relates to the discovery that artiodactyla, and specifically ungulates, and more specifically, cattle, have a homolog (bovine NRAMP1) of the human and murine NRAMP1 gene.

The present invention discloses that this NRAMP1 gene has at least two differing sequences in the 3' untranslated region of the gene that significantly (P=0.0089) associate with either the resistance or susceptibility of an animal containing the sequence to at least the diseases brucellosis, tuberculosis, paratuberculosis and salmonellosis.

Still more particularly, the present invention shows that at least these two different NRAMP1 sequences can be readily differentiated by SSCA or SSCP analysis or any other technique suitable to detect a particular genetic sequence, for example, but not limited to direct sequencing, so that one can easily screen animals for the presence of either a resistance associated sequence or a susceptible associated sequence of NRAMP1.

This information as to whether an animal contains either a resistant associated sequence or a susceptible associated sequence can then be used to predict whether the screened animal is likely to be susceptible or resistant to diseases caused by intracellular parasites such as brucellosis, tuberculosis, paratuberculosis and salmonellosis. According to the screening results of the instant invention, susceptible animals can then be segregated, treated prophylactically or therapeutically, or sacrificed. Resistant animals, on the other hand, can then be safely raised, harvested and/or bred to create disease resistant animals.

Further, according to the present invention, animal breeding for disease resistance can be easily monitored by practicing the genetic screening methods of the invention in order to assay for the transmission of resistance to disease. Further still, the method of the present invention allows for the selective breeding of disease resistant animals based upon the selective tracking of only a single genetic trait and the assaying of that that via genetic analysis, rather than phenotypic selection. This allows for the favorable trait to segregate and be traced independently, allowing for the selective tracing of the favorable genetic sequence, which can avoid unnecessary selection of unwanted traits and allow the simultaneous tracing of other favorable traits.

The invention further relates to the use of the discovered sequences of bovine NRAMP1 as indicated, or "genetic markers," of disease susceptibility or resistance in artiodactyla. Specifically, the invention includes the detection and identification of these specific gene sequences via conventional molecular biological techniques such as, but not limited to, SSCA and SSCP. Still more specifically, the present invention illustrates specific methods and materials (such as, for example, specific PCR primers) for identifying and distinguishing these sequences via SSCA, SSCP or direct sequencing. This allows one to screen an animal and detect which sequences of NRAMP1 the animal possesses, which then allows the accurate prediction of the animal's susceptibility or resistance to disease.

Still further, the present invention relates to the use of these predictive genetic markers in animal husbandry including in food production, and selective breeding of disease resistant animals, including cattle.

The conception of this invention was based, in part, on a series of published reports on genetic selection of swine naturally resistant to swine brucellosis in the 1930's and 1940's. These publications reported that swine which did not produce antibodies to an oral challenge of virulent *Brucella suis* produced offspring that did not produce an antibody to a similar challenge approximately 70% of the time compared to a frequency of approximately 20% for progeny from unselected control groups. Id.

The observation that approximately 20% of unvaccinated control cattle challenged with a virulent strain of *Brucella abortus* S2308 did not exhibit any signs of brucellosis (infection with *Brucella abortus*) and the lack of production of antibodies post-challenge led the inventors to hypothesize that this was a natural resistance to bovine brucellosis. The inventors then began breeding studies to determine if this natural resistance was heritable and to search for genes that could control this natural resistance, if it was heritable. The natural resistance was shown to be heritable as it responded to selection; a greater percentage of offspring were naturally resistant to brucellosis (57% compared to 37%) when a naturally resistant sire was bred to naturally resistant dams than when a naturally resistant sire was bred to naturally susceptible dams.

Genetic studies in other animals indicated a major gene termed Bcg might control this natural resistance to *Mycobacterium bovis*-BCG. A candidate gene in mice was reported (Vidal, et al., 1993). However, unlike the field of the present invention, this report was not in an artiodactyla animal. The inventors then proposed that cattle might possess a conserved homolog of the murine gene and that this conserved homolog might have a major controlling effect over the natural resistance to brucellosis in the cattle the inventors had been breeding.

The inventors then tested the above hypothesis and cloned, sequenced, and genetically mapped bovine NRAMP1 in the bovine. The bovine NRAMP1 was mapped to BTA 2, within syntenic loci conserved on HSA 2q and MMU1. Bovine NRAMP1 is expressed primarily in macrophages and tissues of the reticuloendothelial system, and is predicted to encode a 548 amino acid protein that has 12 transmembrane segments with one hydrophilic N-terminal region containing a Src homology 3 (SH3)-binding motif located at the cytoplasmic surface, and a conserved consensus transport motif. The gene is designated as bovine NRAMP1 because of conserved genetic linkage, tissue expression, and amino acid sequence homology with murine NRAMP1.

The inventors discovered macrophage restricted expression of the bovine NRAMP1 gene, and importantly, discovered sequence and conformational differences in the bovine NRAMP1 gene which significantly associate with natural resistance or susceptibility to brucellosis in cattle. Testing was also conducted to determine if bovine NRAMP1 is conserved in other artiodactyla. Significantly, swine, goats, sheep bison (American Buffalo), llamas, elk (wapiti), red deer, sika deer, water buffalo, follow deer, and white-tailed deer, indeed all artiodactyla (for a definition of artiodactyla, see Nowak, R. M. et al., 1983) analyzed thus far, have a conserved NRAMP1 gene.

The present invention has also shown that cattle whose phenotypes have been ascertained to be resistant to a challenge of virulent *B. abortus* are significantly different in their ability to control the intracellular replication of *Brucella abortus, Mycobacterium bovis*-BCG, and *Salmonella dublin* in an in vitro macrophage killing assay than cattle whose phenotypes have been ascertained to be susceptible (85% correlation with challenge phenotype) (Qureshi, T., Templeton, J. W., and Adams, L. G. 1996).

These cattle were phenotyped both by an in vivo challenge with *Brucella abortus* Strain 2308 and by an in vitro macrophage killing assay of *Brucella abortus* Strain 2308, *Mycobacterium bovis*-BCG strain and *Salmonella dublin* to determine their resistance or susceptibility to bovine brucellosis and tuberculosis. Using SSCA or SSCP, a genetic polymorphism was discovered in the 3' UTR of the gene. This polymorphism has two different forms which significantly associate (p=0.0089) with naturally resistant and naturally susceptible phenotypes to bovine brucellosis, tuberculosis, salmonellosis, and paratuberculosis in unrelated cattle.

By screening for the particular polymorphism and/or sequence that a given animal has, one can accurately and efficiently predict the susceptibility, or resistance of that animal to ruminant brucellosis, tuberculosis, paratuberculosis and salmonellosis and other diseases involving intracellular parasites of macrophages.

The bovine NRAMP1 gene is conserved in Bos spp. Bison bison, *Odocoileus virginianus, Capra hirus, Alces alces, Cervus canadensis, Cervus elaphus, Dama dama, Elaphurus davidianus,* Ursus spp. Sus scrofa, and *Oreamnos americanus* (SEQ ID NOs. 16–27, respectively) and most likely all domestic and wild artiodactyla (see FIGS. 8A1 and 8A2 SEQ ID Nos. 16–27, FIG. 8C, and FIG. 8D). In addition, the Nramp1 protein is also highly conserved (see, for example, FIG. 8B SEQ ID Nos 9 and 28). The discovered genetic variation in the 3' UTR of the NRAMP1 gene of artiodactyla can be used, inter alia, in selecting and breeding domestic and free-ranging artiodactyla that are resistant to, inter alia, brucellosis, tuberculosis, paratuberculosis and salmonellosis (see FIG. 8D, SEQ ID Nos. 29 and 30).

The bovine NRAMP1 polymorphism results from a transversion at position 1782 of the bovine NRAMP1 cDNA; thymine in the resistant sequence to guanine in the susceptible sequence. Additionally, there is a polymorphic DNA microsatellite sequence difference between resistant and susceptible cattle involving the number of (GT) dinucleotide repeats and spacing in the 3' UTR of bovine Nramp1. This sequence in resistant animals, beginning at position 1779, is:

SEQ ID NO 15: $GGGTGT(GT)_{10}AT(GT)_3(N)_{61}(GT)_5(N)_{24}(GT)_{13}$ where "N" symbolizes any one of the four nucleotide bases A, C, G or T. In contrast, the DNA sequences associated with susceptible cattle follow the form:

SEQ ID NO: 32: $(GT)_{<10}AT(GT)_3(N)_{>61}(GT)_5(N)_{<24}(GT)_{>13}$ where "N" again symbolizes any one of the four nucleotide bases A, C, G or T The detection of the resistance associated sequence or the susceptible associated sequence can be done by SSCA, SSCP, polymerase chain reaction (PCR) followed by direct DNA sequencing or any other technique known to those of skill in the art capable of detecting genetic sequence differences. The sequence of PCR primers used to detect the genomic DNA sequence of the bovine NRAMP1 which contains the polymorphic DNA sequences associated with resistance or susceptibility are indicated in FIG. 1A, SEQ ID Nos 1 and 2. These PCR primers will amplify the resistant and susceptible allelic sequences in genomic (g) or cDNA. However, it should be stated that any PCR primers that will amplify the polymorphic region can also be used in this invention.

In one screening trial (see FIG. 3, for example), the bovine NRAMP1 sequences correctly identified animals as being either resistant or susceptible in 18 of 22 cattle naturally resistant or susceptible to brucellosis (FIG. 3A and FIG. 3B) (Significant association, p=0.0089, Fisher's exact analysis). Importantly, these 22 cattle were all unrelated animals.

The bovine NRAMP1 sequences can be detected in gDNA isolated from any tissue including gDNA isolated from, but not limited to, peripheral blood samples, semen, mucosal scrapings, etc. using PCR amplification.

As shown in Example 9, for example, approximately 82% of the cattle naturally resistant or susceptible to brucellosis and tuberculosis can be identified by typing them for the bovine NRAMP1 resistant or susceptible polymorphism by using SSCP (or SSCA). The zygosity of cattle for the resistant associated polymorphism (heterozygote or homozygote genotype) can be determined and a breeding program can be practiced to efficiently produce cattle naturally resistant to brucellosis and tuberculosis. Additionally, the bovine NRAMP1 gene is a good candidate gene for production of transgenic animals which possess genes for outstanding production traits and by transgene action are naturally resistant to, inter alia, brucellosis, salmonellosis, paratuberculosis, and tuberculosis.

The genetic selection of breeding animals for a single locus is not detrimental to overall animal production i.e. beef, muscle, grain or milk production, as long as a breeding plan is constructed to buffer this effect. All of the other chromosomes will segregate by independent assortment and will perpetuate heterozygosity. Additionally, with the current availability of microsatellite markers spaced throughout the bovine genome, selection for disease resistant genotypes can now be achieved without compromising other desirable production traits while maximizing heterozygosity at approximately 100 microsatellite loci. With the development of the bovine gene map and the identification of major genes controlling economically important traits in cattle and other livestock, the ability to identify a prized genotype of disease resistance and high quality production will be possible in the near future. Tremendous progress in cattle breeding will be realized when it is possible to select for superior genotypes directly by identifying important genes. The SSCP or SSCA based detection of NRAMP1 polymorphic sequences can be conducted on gDNA isolated from antemortem or postmortem tissues, provided the postmortem tissue has been reasonably protected from a DNA degrading environment where autolysis of the tissue would occur.

In a preferred embodiment, one mode for the detection of the artiodactyla NRAMP1 sequences is in a laboratory with routine DNA isolation, DNA PCR amplification, electrophoresis technique, SSCA, SSCP analysis, direct DNA sequencing or any other technique suitable for detecting differences in genetic sequences.

In a preferred embodiment, one mode for identification of the artiodactyla NRAMP1 resistant and susceptible associated sequences is by specific PCR amplification of gDNA isolated from an individual animal's peripheral blood collected in an anticoagulant. The PCR amplification can performed in an ordinary laboratory with capabilities of performing the polymerase chain reaction and ordinary expertise in molecular biology. With hand-held thermal cyclers it is also possible to perform the PCR amplification of the alleles outside the laboratory in a so-called "chute-side" assay shortly after the blood is collected.

Figure 3C:
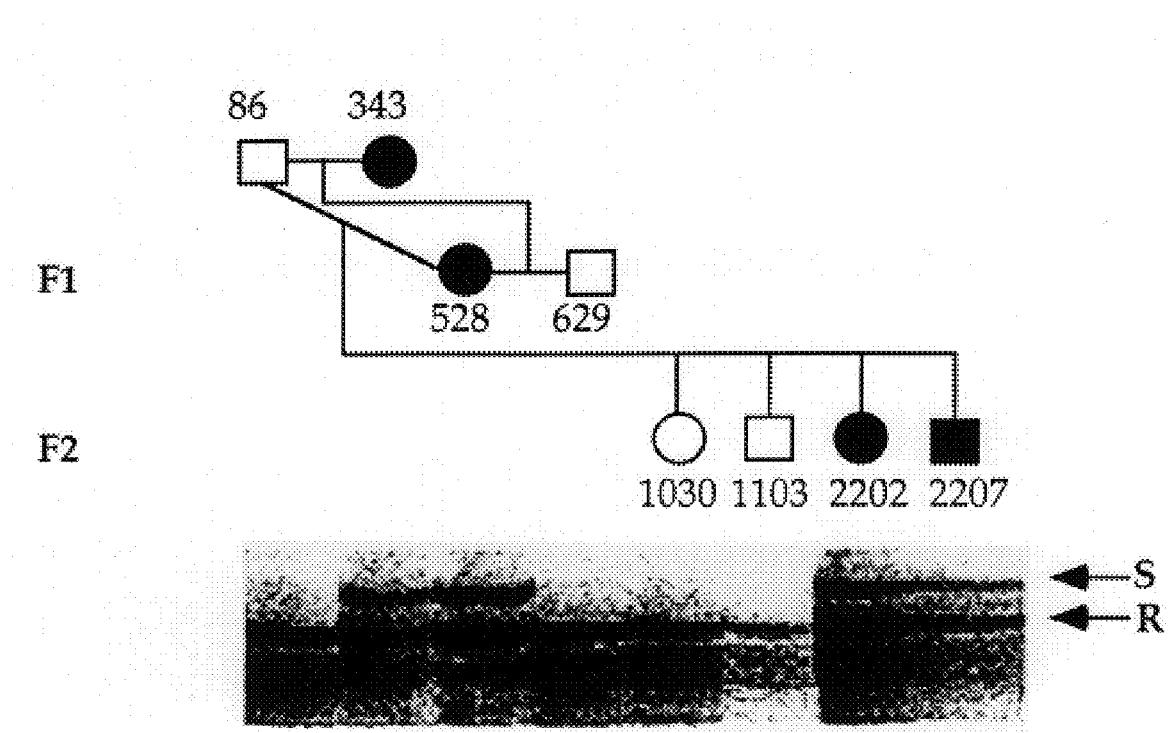
FIG. 3C shows the SSCP analysis and pedigree of naturally resistant bull sired to a naturally susceptible cattle and their progeny.
Figure 5:
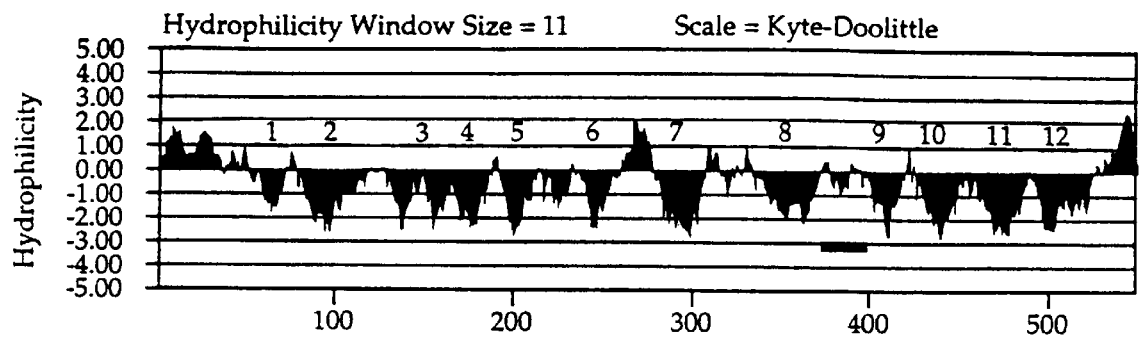
FIG. 5 shows the hydrophobicity profile of the predicted amino acid sequence of bovine NRAMP1.

In a preferred embodiment, one mode for utilizing the present invention in detecting the NRAMP1 resistant and susceptible sequences is by a PCR amplification of gDNA isolated from peripheral blood of individual artiodactyla animals followed by SSCA or SSCP analysis of the PCR product. The isolation of the gDNA from blood cells can be done by standard methods suitable for subsequent PCR amplification. As shown in Example 8 and FIG. 1A, PCR primer sequences can be used to amplify the polymorphic DNA region of both resistant and susceptible animals, namely cattle. PCR products can be specifically labeled, either by using radioactive nucleotides in the PCR reaction (as in the case of SSCA) or by using a specifically end-labeled primer (as in the case of SSCP analysis) in the PCR reaction. It should be stated that other radioactive (i.e. $^{32}$P, $^{33}$P, etc.) or non-radioactive alternatives (for example, but not limited to DIG-labeling) can be used to specifically label the PCR products. These amplicons can then be run on a polyacrylamide gel and the migration of the amplicons visualized by standard autoradiographic techniques. It should be noted that if, for example, non-radioactive labeling techniques are used, alternative detection methods can also be employed. Susceptible-associated and resistance-associated DNA sequences can be readily distinguished (FIG. 3A). The banding patterns of amplicons from resistance-associated and susceptible-associated DNA are quite different; the amplicons from resistance-associated DNA sequences show faster migration through the gel as is expected from their smaller size amplicons (175 bp for resistance associated amplicons vs. >175 bp for susceptible associated amplicons).

One primary advantage of a diagnostic test using SSCA or SSCP analysis is that this technology is readily available. It is relatively simple compared to many techniques used to identify DNA sequences; it is relatively inexpensive to equip a laboratory With the necessary equipment; it is conducive technology for mass through-put of large numbers of samples; and the relatively simple technology yields in minimal false (positive or negative) test results when properly controlled. Further, because the resistance and susceptibility associated sequences are genetic, they are transferable, meaning, for example, resistance can be a heritable trait. Since the transmission of these diseases is dependent on a susceptible host, resistant animals offer an excellent opportunity to break the cycle of disease spread and begin eradication.

There are no particular unique disadvantages to the proposed SSCA or SSCP analysis based assay compared to other molecular biologic diagnostic tests. All such tests require some specialized equipment, a laboratory utilizing basic good laboratory practices and at least currently, tissue (blood) collection and transportation to a laboratory. The occasional stress associated with restraining an animal for blood collection will not effect the test results.

Figure 6:
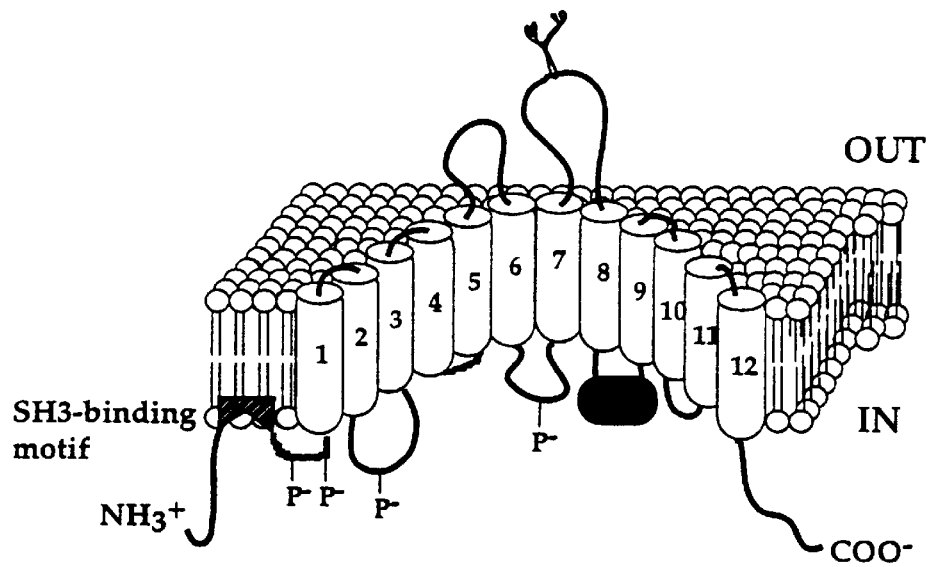
FIG. 6 shows a schematic representation of the putative structure of the bovine Nramp1 protein.

A major purpose of this invention is to identify sequences of NRAMP1 associated with resistance or susceptibility to disease, using SSCA or SSCP-based techniques which results in correctly identifying artiodactyla that are naturally resistant to brucellosis, tuberculosis, salmonellosis, and paratuberculosis with a high degree, for example 82%, of accuracy.

There are several possibilities which could account for the lack of 100% SSCP association with resistant phenotypes. It is possible that Bcg is not a single gene but a gene complex and NRAMP1 is one of the Bcg genes, or there are two or more genes controlling natural resistance to bovine brucellosis. Alternatively, NRAMP1 may be in linkage disequilibrium Faith the Bcg gene and is a marker gene for the $Bcg^{r\ or\ s}$ alleles. The lack of 100% association of the bovine NRAMP1 SSCP with the natural resistant or susceptible phenotypes could also be due to incorrect ascertainment of some of the true cattle R or S phenotypes caused by genetic heterogeneity, phenocopies, lack of penetrance, or error in the challenge procedure. We attempted to minimize effects of phenocopies by a uniform, potent challenge (conjunctival instillation of $10^7$ colony forming units of virulent *B. abortus*). An indication that lack of penetrance is not a major problem is the fact that the phenotypes of the founders respond to genetic selection in breeding studies (Templeton et al. 1990a; Templeton et al. 1990b). The fact that the cattle used in these studies are derived from four different breeds implies genetic heterogeneity does not confound the phenotypes and provides strong, direct evidence that NRAMP1 is a likely candidate for a major gene controlling natural resistance to, inter alia, brucellosis, and in particular bovine NRAMP1 is a likely candidate for a major gene controlling natural resistance to, inter alia, bovine brucellosis.

The following Examples are intended to illustrate the embodiments of the present invention and are not in any way intended to limit the scope of the invention in any manner.

EXAMPLE 1

Cloning of Bovine NRAMP1 and Isolation of Bovine NRAMP1 cDNA

The bovine NRAMP1 gene was cloned as follows. Based on the genomic sequence of murine NRAMP-1, oligonucleotide primers SEQ ID NO. 3 and SEQ ID NO. 4 (also designated as 1F and 1R) were used to amplify a 155 bp segment in bovine genomic DNA (FIG. 1B).

From this 155 bp bovine sequence, RT-PCR was performed on bovine macrophage mRNA, using a bovine specific forward primer designated SEQ ID NO. 5 (PE2): 5' CGTGGTGACAGGCAAGGACT3' and a reverse primer, SEQ ID NO. 6 (MUT2): 5' CCAAGAAGAGGAAGAAGAAGG-TGTC3' from the murine NRAMP1 cDNA sequence (Vidal et al. 1993).

Reverse transcription was performed as follows. Total RNA was extracted from bovine macrophage, spleen, lung, or heart as described (Chirgwin et al. 1979). 0.5 μg total RNA was transcribed in 25 μl reaction at 37° C. for 60 min. with MMLV reverse transcriptase (Gibco-BRL). cDNA amplification was performed at 95° C. (5 min) followed by 32 cycles of 94° C. (1 min), 58° C. (1 min), and 72° C. (1 min) with 1 mM $MgCl_2$, 2 μl 10×PCR buffer, 2 Units Taq polymerase (Perkin-Elmer) and 4 μl RT template in a final volume of 25 μl.

A 222 bp product was amplified from reverse transcribed bovine macrophage total RNA. Sequence analysis showed that this PCR product contained 90% nucleotide identity with the third exon (nucleotide positions 338–458) of the murine homolog. The 222 bp product was generated to screen a bovine splenic λgt11 cDNA library (Clontech). A total of $1\times10^6$ clones were screened by in situ plaque hybridization with radiolabeled [$^{32}$P]-α-dCTP (3000 Ci/mmol) (Dupont, NEN Research Products) by hexamer priming ($1–3\times10^9$ cpm/μg)(Feinberg et al., 1983). Filters were washed under conditions of increasing stringency up to 1×SSC, 0.1% SDS at 65° C. for 30 min. Positive clones were verified using PCR with primers SEQ ID NO. 5 (PE2) and SEQ ID NO. 6 (MUT-2) and subsequently PCR amplified to obtain a 2.3 kb insert with λgt11 insert screening amplimers. This PCR product was gel purified and ligated into pT7BlueT-Vector (Novagen). Both strands of plasmid DNA were sequenced by the dideoxy method of Sanger et al. (Sanger et al. 1977) using modified T7 DNA polymerase (USB) and [$^{35}$S]-α-dATP (3000 Ci/mmol) (NEN Research Products, Boston, Mass.). All sequence data were compiled and analyzed using MacVector 4.1 software (Eastman Kodak Comp. New Haven, Conn.).

Twenty potentially full-length NRAMP1 clones(≈2.3 kb) were obtained, eight of which were sequenced and used to construct the complete sequence. As shown in FIG. 4, the in-frame initiator codon ATG is located at nucleotide position 73 from the 5'-end, and is followed by a segment of 1644 nucleotides, forming a single open reading frame (ORF) encoding a protein of 548 residues with a calculated molecular weight of 59.6 KDa. A TGA termination codon located immediately dowvnstream from glycine 548 (nucleotide pst 1717) is followed by an intact AATAAA polyadenylation signal, position 2257.

EXAMPLE 2

Analysis of the Predicted Bovine NRAMP1 Structure

Note that as used herein, it is understood that the term "NRAMP1" includes the coding sequence and at least the 3' UTR of the gene. The first 64 N-terminal amino acids of Bovine NRAMP1 are rich in proline (11/64), glycine (10/64), serine (8/64), and charged amino acids (10/64), and include two putative PKC phosphorylation sites at amino acid positions 37 and 51 (FIG. 2). Because SH3 domains interact specifically with proline-rich peptides, we compared the proline-rich coding fragment PPSPEP (positions 21–26) to several identified SH3- binding sequences (Lim et al. 1994). The analysis revealed that the "PNNP" binding motif (Musacchio et al. 1994) is conserved in bovine Nramp1, which indicates that bovine Nramp1 contains an N-terminal SH3 binding domain. Kyte-Doolittle hydrophilicity analysis (FIG. 5) disclosed that the surface probability of peptide PPSPEP is from 50.3% to 67.6%, which indicates that the bovine Nramp1 SH3-binding motif is most likely located at the inner membrane surface.

Analysis of the remaining bovine NRAMP1 indicates the predicted protein to be highly hydrophobic with 12 putative transmembrane domains (FIG. 6) in agreement with the murine and human Nramp1 putative structure (Vidal et al. 1993; Barton et al. 1994; Cellier et al. 1994). The bovine NRAMP1 gene product contains one potential N-linked glycosylation site at position 335, within a highly hydrophilic region between predicted transmembrane (TM) domains 7 and 8, and three PKC phosphorylation sites on serine (positions 37, 51, and 269, respectively). A 20 amino acid transport motif is located between the predicted TM domains 8 and 9 and conserved in murine and human Nramp1 (FIG. 2). This conserved motif is known as the "binding-protein-dependent transport system inner membrane component signature" (Vidal et al. 1993; Malo et al. 1994a; Cellier et al. 1994; Malo et al. 1994b). Based on the hydropathic analysis and conversed transport motif, we propose, but not in a limiting sense, that the membrane-associated topography of bovine Nramp1 (FIG. 6) is as follows: the NH2-terminus is located in the cytoplasm, and the following 12 TM domains result in 5 consecutive transmembrane loops. This arrangement would place the SH3-binding motif on the cytoplasmic membrane surface; SH3-binding domain with two potential phosphorylation sites and the transmembrane (TM) loops 2 and 3 and the TM 6 and TM 7 loops containing one phosphorylation site each, all projecting into the cytoplasm; the TM 7 and TM 8 loop containing one predicted N-linked extra-cellular glycosylation site; and the carboxyl terminus in the cytoplasm.

EXAMPLE 3

Homology Among Human, Murine, and Bovine Nramp Proteins

Comparison of human, murine and bovine predicted Nramp protein sequences (FIG. 2) indicates a remarkable degree of homology (86.9% amino acid sequence identity between murine and bovine; 88.6% amino acid sequence identity between human and bovine). The predicted TM segments 1–8 are highly conserved hydrophobic membrane associated domains in the three species, with 99% identity between human and bovine, and 96% identity between murine and bovine. The most conserved consecutive region is from TM 8–9 with 100% identity from position 346 to 456 between human and bovine; 98.2% identity between murine and bovine. Within the TM 8–9 segment, the bovine "binding protein dependent transport system inner membrane component signature" was identical with murine and human Nramp with one exception (substitution of lysine to arginine at position 392 in the human (FIG. 2). Also among these three species, one predicted N-linked glycosylation site was conserved within the fourth putative extracellular loop between TM 7 and 8; and one consensus PKC phosphorylation site was conserved in the predicted intracytoplasmic loop between TM 6 and 7 at position 37 (FIG. 2) (Vidal et al. 1993; Cellier et al. 1994; Gruenheid et al. 1995).

Amino acid substitutions were not randomly distributed along the sequence of the protein but were significantly clustered within certain regions. The most striking differences were located at extreme ends of the proteins, NH2 terminus (57.4% identity of positions 1–47 between murine and bovine; 66% identity of positions 1–50 between human and bovine) and COOH-terminus (57.6% identity of positions 516–548 between murine and bovine; 69.6% identity between human and bovine). The predicted third and fourth extracellular loops at positions 215–237 and positions 307–346 were less conserved in amino acid sequences than the TM domains. Identity was 78.2% between murine and bovine and 82.0% between human and bovine for the predicted third extracellular loop, respectively, and 75.0% identity between murine and bovine and 85% identity between the human and bovine, respectively, for the predicted fourth extracellular loop.

EXAMPLE 4

Genetic Mapping of Bovine NRAMP1

Genetic Mapping was performed as follows. Bovine-hamster hybrid somatic cell panel blots (Womack et al. 1986; Adkinson et al. 1988; Beever et al. 1994) were hybridized with the 1F/1R PCR generated probe ($4-8\times10^8$ cpm/μg) (Feinberg et al. 1983). Hybridization was performed at 43° C. for 18 hrs in 20 ml of 50% formamide, 5×SSC, 1×Denhardt's solution, and 20 mM NaPO$_4$ (pH-6.8), followed by washing once in 2×SSC, 0.5% SDS at room temperature for 15 min., two successive washes in 1×SSC, 0.1% SDS at 65° C. for 30 min (Adkinson et al. 1988). All gene probes were labeled with the random primed DNA labeling method is α-[$^{32}$P] dCTP (3000 Ci/mmol) (NEN Research Products, Boston, Mass. (Feinberg et al. 1983). Synteny was ascertained by analysis of concordancy of the probe with known marker genes as described (Womack et al. 1986; Adkinson et al. 1988; Womack et al. 1994).

Figure 9:
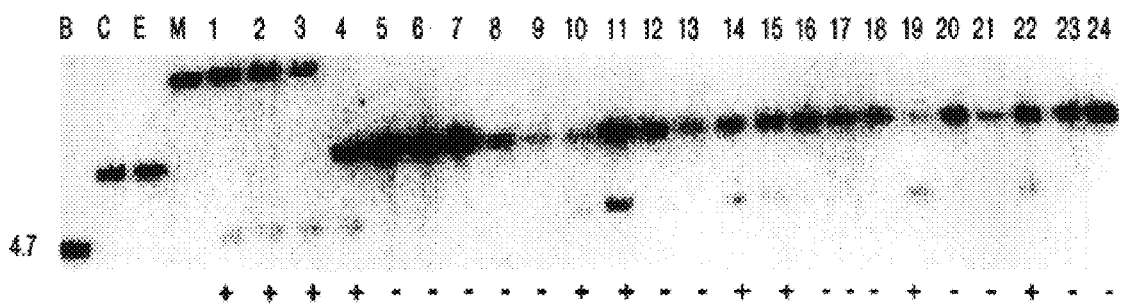
FIG. 9 shows the genetic mapping of bovine NRAMP1 on BTA2.
Figure 10:
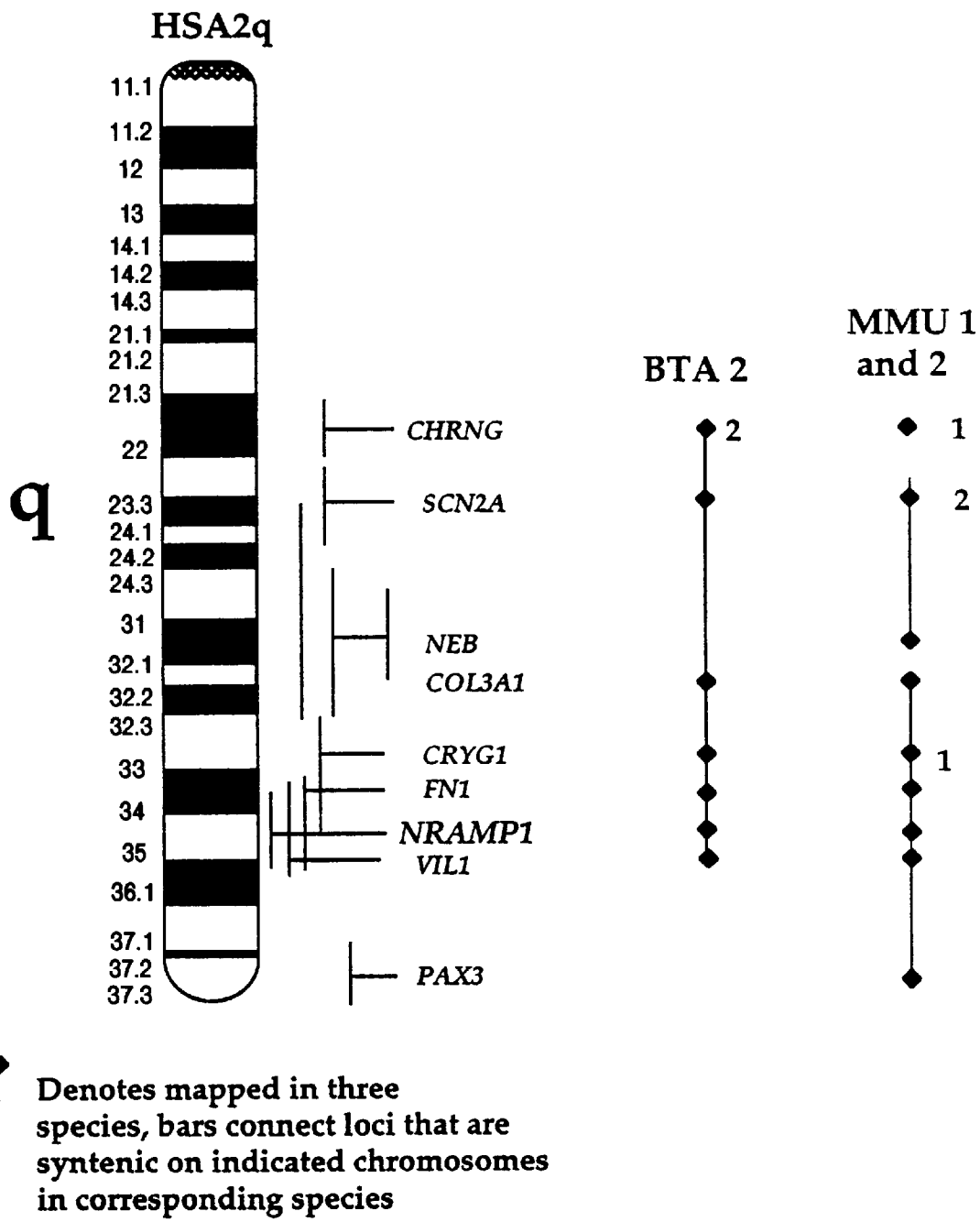
FIG. 10 shows a representation of the conserved chromosomal segments among three species around the NRAMP1 locus.

The syntenic arrangement of bovine NRAMP1 was determined using somatic cell hybrid segregation analysis (Womack et al. 1986; White et al. 1994). DNA from 87 bovine/rodent somatic hybrid cells was digested with Hind III and hybridized to a PCR generated probe using SEQ ID NO. 3 and SEQ ID NO. 4 (1F and 1R) primers (FIG. 1B). The bovine specific Hind III restriction fragment of 4.7 kb was easily discriminated from fragments representing the hamster and mouse homologs, permitting detection of bovine-specific fragments in each cell line. A pairwise concordancy analysis indicated that bovine NRAMP1 segregated 100% concordantly with Cry-γ, which has been assigned to BTA 2 (FIG. 9). An analysis of 87 somatic hybrids revealed that 28 were positive and 59 were negative for both Cry-γ and bovine NRAMP1. A group of bovine syntenic loci, villin, Cry-γ (Adkinson et al. 1988; Beever et al. 1994) and Interleukin-8 receptor has been mapped to a region of BTA 2 and conserved on HSA 2q (White et al. 1994) and proximal MMU 1 (Cerretti et al. 1993), which were closely linked to the Lsh/Ity/Bcg locus in the mouse (FIG. 10). These results further support the homology among human, bovine and murine NRAMP.

EXAMPLE 5

Single-stranded Conformational Analysis (SSCA)

We have identified cattle phenotypically resistant and susceptible to brucellosis by in vivo challenge (Harmon et al. 1985). Screening of 22 outbred, unrelated individuals by SSCA revealed the existence of two general single stranded polymorphic forms of bovine NRAMP1 (FIG. 3A). Sequencing analyses of the PCR-amplified fragments showed a microsatellite length polymorphism starting at position 1785 of two types; one being SEQ ID NO. 31: SEQ ID NO: 32: 5' $(GT)_{10}AT(GT)_3(N)_{61}(GT)_5(N)_{24}(GT)_{13}$ 3'. The other being $(GT)_{<10}AT(GT)_3(N)_{>61}(GT)_5(N)_{<24}(GT)_{>13}$ where "N" symbolizes any one of the four nucleotide bases A, C, G or T (FIG. 7A). These polymorphisms correlate both with their distinctive patterns analyzed by SSCA or SSCP and with their respective in vivo phenotypes [p=0.0089, Fisher's Exact Analysis]. We will designate the former DNA sequence as SSCP$^r$ and the latter sequence as SSCP$^s$. The relative risk (RR) of susceptibility, if an animal possess the SSCP$^s$ is 4.5.

EXAMPLE 6

Cell Specific Expression of Bovine Nramp1-1 mRNA

Figure 11:
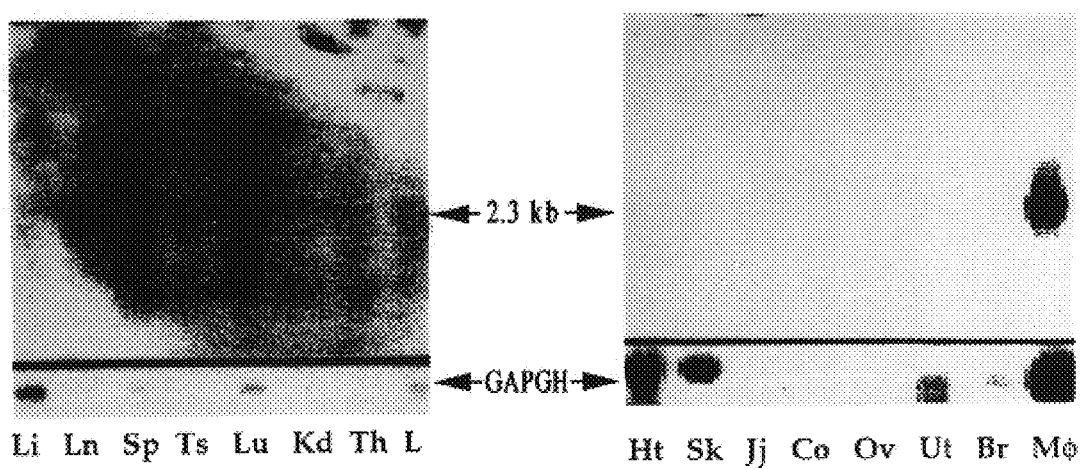
FIG. 11 shows a northern blot analysis of RNA isolated from bovine tissues and cells.

To test whether bovine NRAMP1 was expressed primarily in macrophage populations, we analyzed total RNA prepared from 15 different bovine tissues (peripheral blood lymphocytes, liver, lymph node, spleen, tonsil, lung, kidney, thymus, heart, skeletal muscle, jejunum, colon, ovary, uterus, brain and cultured macrophages) by northern blot analysis using a SEQ ID NO. 3 and SEQ ID NO. 4 PCR generated bovine DNA probe (FIG. 11).

Northern blot analysis was performed as follows. Monocyte-derived macrophages were harvested and cultured as described (Campbell and Adams 1993). Total RNA was isolated from these macrophages and lymphocytes using standard techniques (Chirgwin et al. 1979). 10 μg of total RNA from macrophages and lymphocytes were separated on 1% formaldehyde agarose gels, transferred to Nytran plus membranes (Schleicher & Schuell). Blots were prehybridized in 20 ml of 50% formamide, 10% dextran sulfate, 4.7×SSPE (1×SSPE is 10 mM sodium phosphate, 1 mM EDTA, 150 mM NaCl), 0.47×Denhardt's solution, 0.1% SDS, 0.18 mg/ml heat-denatured salmon sperm DNA, and 0.34% fat free milk for 4 hrs at 42° C. Hybridization at 42° C. for 18 hrs was performed in the same solution containing 2×10$^8$ cpm/ml [$^{32}$P]-radiolabeled probe SEQ ID NO. 3 and SEQ ID NO. 4 fragment. Final wash conditions were 0.2×SSC, 0.1% SDS at 68° C. for 30 min.

A band of approximately 2.3 kb was detected in macrophage, spleen and lung RNA, but was absent in the RNA analyzed from other tissues. These results indicate that bovine Nramp1 is principally expressed in the macrophage and the reticuloendothelial (RE) system.

EXAMPLE 7

Identification of Animals Naturally Resistant or Susceptible to Disease (traditional method)

Cattle were phenotyped for resistance or susceptibility by both in vivo challenge experiments with *Brucella abortus* Strain 2308 and by an in vitro macrophage killing assay.

In vivo assays: Unvaccinated control cattle were challenged with a virulent strain of *Brucella abortus* S2308. Those not exhibiting any signs of brucellosis, bacteriologically culture negative for *B. abortus*, and lacking production of anti-lipopolysaccharide *B. abortus* antibodies post-challenge were considered naturally resistant. Those exhibiting signs of brucellosis, bacteriologically *B. abortus* culture positive, or producing anti-lipopolysaccharide *B. abortus* antibodies post-challenge wvere considered naturally susceptible (Harmon et al. 1985).

In vitro assays: Macrophages from unvaccinated control cattle were isolated according to standard techniques and subsequently challenged weith *B. abortus* in an in vitro assay (Harmon et al. 1989; Price et al. 1990; Campbell et al. 1992). The macrophages from those cattle that were able to control intracellular replication of *B. abortus* in vitro were considered resistant, while the macrophages from cattle that were not as good at controlling intracellular replication of *B. abortus* in vitro were considered susceptible.

EXAMPLE 8

Single Stranded Conformational Analysis (SSCA):

In a total PCR reaction of 15 $\mu$l used for SSCA, inventors mixed 0.2 mM each dGTP, dGTP, dCTP, 0.07 mM dATP, 1 mM $MgCl_2$, 10×M PCR buffer, 0.2 Units of Taq DNA polymerase (Cetus-Perkin Elmer), and 8 $\mu$Ci of [$^{35}$S]-dATP with 50 ng genomic DNA. Parameters for PCR amplification were a single denaturation step of 5 min at 94° C. followed by 32 cycles of denaturation (1 min at 94° C.), annealing (40 sec at 60°) and extension (1 min at 72° C.), and a final extension step of 7 min at 72° C. The oligonucleotide primers designed from 3'-UT were SEQ ID NO. 1 (Fmicrol)=5' AAGGCAGCAAGACAGACAGG3', nucleotide positions 1814–1833 and SEQ ID NO. 2 (3end3)=5' ATGGAACTCACGTTGGCTG3', nucleotide positions 1970–198). The SSCA polymorphisms of 22 unrelated cattle were detected by separating these 175 bp PCR fragments on 6% polyacrylamide gels with or without urea at room temperature at 90 W for 2.5 hr.

SSCP Analysis:

SSCP was performed essentially the same as SSCA with the following two exceptions. First, for SSCP analysis, either SEQ ID NO. 1 or SEQ ID NO. 2 was end-labeled prior to the PCR reaction rather than having [$^{35}$S]-dATP in the PCR reaction mix. Second, for SSCP analysis, the polyacrylamide gels always contained urea.

EXAMPLE 9

Specific Genetic Sequences Associated with NRAMP1 in situ

Significantly Associate with Resistance or Susceptibility to Ruminant Brucellosis, Tuberculosis, Paratuberculosis and Salmonellosis The cattle used in these experiments are all unrelated. One is a purebred Angus (*Bos taurus*) and other twenty two are cross bred cattle produced by a three-way cross—$F_1$ [Jersey (*Bos taurus*)×American Brahman (*Bos indicus*)] (Harmon et al. 1985). All animals used in experiments were housed in USDA-approved facilities with daily supplemental feeding. All experimental protocols are University reviewed and approved.

PCR amplification of DNA isolated from susceptible or resistance cattle was performed as follows. In a total PCR reaction of 15 $\mu$l used for SSCA, 0.2 mM dGTP, dTTP and dCTP, 0.07 mM dATP, 1 mM $MgCl_2$, 1.5 $\mu$l 10×PCR buffer, 0.2 Units of Taq DNA polymerase (Cetus-Perkin Elmer), and 8 $\mu$Ci of [$^{35}$S]-dATP were added to 50 ng of genomic DNA. Parameters for PCR amplification were a single denaturation step of 5 min at 94° C. followed by 32 cycles of denaturation (1 min at 94° C.), annealing (40 sec at 60° C.) and extension (1 min at 72° C.), and a final extension step of 7 min at 72° C. The oligonucelotide primers designed from the 3' UTR were SEQ ID NO. 1 and SEQ ID NO. 2 (FIG. 1A). This amplified DNA was then subjected to gel electrophoresis under SSCA or SSCP conditions. Namely, the PCR fragments were run on a 6% polyacrylamide gel (National Diagnostics, G.A.) at room temperature at 90 W for 2.5 hrs. The different migration patterns of the amplified DNA under these gel conditions correlated with the phenotype of the cattle previously determined by in vivo or in vitro challenge experiments with *B. abortus* (Harmon et al., 1985). PCR amplification of DNA (using SEQ ID NO. 1 and SEQ ID NO. 2 as primers) from cattle previously determined to be resistant produced an amplicon that migrated faster than the DNA isolated and amplified from cattle determined to be sensitive when said amplicons were run on a 6% polyacrylamide gel under said conditions (FIG. 3).

Subsequent sequencing of the amplicons from some of these cattle revealed two significant sequence differences (FIG. 7A). These sequence differences correlated with in vivo determined resistance/susceptibility and can be categorized into two general groups. The DNA amplified from resistant cattle corresponds to DNA sequences of the type (SEQ ID NO. 15):

GGGTGT(GT)$_{10}$AT(GT)$_3$(N)$_{61}$(GT)$_5$(N)$_{24}$(GT)$_{13}$ whereas the DNA amplified from susceptible cattle corresponds to DNA sequences of the type, SEQ ID NO: 33: GGGGGT(GT)$_{<10}$AT(GT)$_3$(N)$_{>61}$(GT)$_5$(N)$_{<24}$(GT)$_{>13}$ Although SSCA and SSCP cannot determine the exact DNA sequence of the cattle in this region, the differences in migration patterns of the susceptible and resistant-associated amplicons allow us to define said amplicons as being SSCP$^r$ or SSCP$^s$ for single stranded conformation polymorphism of the resistant or susceptible type, respectively.

In addition, because of the conserved nucleotide sequence among swine, goats, sheep, bison (American buffalo), llamas, elk (wapiti), red deer, silka deer, water buffalo, fallow deer, white-tailed deer, and most likely all domestic and wild artiodactyla in this region, we can expect these same sequence differences and their relationship to disease susceptibility to be applicable to all artiodactyla (see, FIGS. 8A1, 8A2, 8C, and 8D). In this regard, the intracellular survival of *Brucella abortus* and *Mycobacterium bovis* BCG was determined in an in vitro monocyte-derived macrophage killing assay using macrophages from Bison phenotypically determined to be naturally resistant or susceptible to *Brucella abortus* infection, see Table 1.

TABLE 1

Intracellular Survival of *Brucella abortus* and *Mycobacterium bovis* BCG in an in vitro Monocyte-derived Macrophage Killing Assay Using Macrophages from Bison Phenotypically determined to be naturally resistant or susceptible to *Brucella abortus* Infection

| | % Survival[2] | |
| --- | --- | --- |
| Bison Number | B. abortus | M. bovis BCG |
| 1-R[1] | 81% | 75% |
| 2-R | 84% | 84% |
| 3-R | 64% | 77% |
| 4-R | 86% | 76% |
| 5-R | 93% | 87% |
| 6-R | 59% | 87% |
| 7-S[1] | 123% | 121% |
| 8-S | 120% | 125% |
| 9-S | 110% | 123% |
| 10-S | 150% | 200% |

[1]The R and S designates bison phenotypically determined to be naturally resistant (R) or susceptible (S) to *Brucella abortus*. This was determined by a challenge of a not previously exposed, either by natural exposure or vaccination, pregnant bison at mid-gestation with 1 × 10$^7$ virulent *B. abortus* organisms.
[2]Percent survival refers to the number of *B. abortus* organisms that survive after being phagocytosed by the macrophages compared to the numbers of bacteria at Time 0 after 3 days of culture for the *B. abortus* and 14 days of culture for the *M. bovis* BCG.

In addition, these in vitro phenotypically determined resistant/susceptibility profiles of bison were compared with the genotypically determined resistant/susceptibility profiles determined from the 3' UTR of the bison NRAMP1 gene. Similar to the bovine studies, a correlation between the sequence at the 3' UTR of bison NRAMP1 and the resistance/susceptibility phenotype exists. The bison phenotypically determined to be resistant, had a resistance-associated gene sequence at the 3' UTR, while the bison phenotypically determined to be susceptible, had a susceptible-associated gene sequence at the 3' UTR (FIG. 8D).

FIG. 8D shows the NRAMP1 cDNA sequences of the 3' UTR in naturally susceptible and resistant bison. Nucleotides are numbered positively in the 5' to 3' orientation to the right of each lane, starting with the coding nucleotide G at 1676 and ending with the last nucleotide. Stop code ATG is indicated by (@). Three TG repeats including (TG)13, (TG)8, and (TG)16 are bolded, separately. The differences between the R and S nucleotide sequences are the S sequence has one less TG in the first repeat (TG)12 versus (TG)13 and is therefore two bases shorter overall (2259) versus (2261) for this area of the NRAMP1 3' UT sequence. the Polymorphisms containing the first (TG) 13 were detected by SSCA using primers Fmicro and Bmicro1' as indicated.

REFERENCES

1. Adkison, L. R., Leung, D. W., Womack, J. E. Somatic cell mapping and restriction fragment analysis of bovine alpha and beta interferon gene families. *Cytogenet. Cell Genet.* 47, 62–65 (1988).
2. Barton, C. H., White, J. K, Roach, T. I. A., Blackwell, J. M. NH2-terminal sequence of macrophage-expressed natural resistance-associated macrophage protein (Nramp) encodes a proline/serine-rich putative Src homology 3-binding domain. *J.Exp. Med.* 179, 1683–1687 (1994).
3. Beever, J. E., Da, Y., Ron, M., Lewin, H. A. A genetic map of nine loci on bovine Chromosome 2. *Mamm. Gen.* 5, 542–545 (1994).
4. Blackwell, J. M., Barton, C. H., White, J. K., Roach, T. I. A., Shaw, M. A., Whitehead, S. H., et al. Genetic regulation of leishmanial and mycobacterial infections: the Lsh/Ity/Bcg gene story continues. *Immunol. Lett.* 43, 99–107 (1994).
5. Blackwell, J., Roach, T. I. A., Atkinson, S. E., Ajioka, J. W., Barton, C. H., Shaw, M. Genetic regulation of macrophage priming/activation: the Lsh gene story. *Immunol. Lett.* 30, 241–248 (1991).
6. Cameron, H. S., E. H. Hughes, and P. W. Gregory Genetic resistance to brucellosis in swine. *J Anim Sci.* 1:106–110 (1942).
7. Cameron, H. S., E. H. Hughes, and P. W. Gregory Studies on genetic resistance in swine to Brucella infection. Preliminary Report. Cornell Vet. 30:218–222 (1940).
8. Campbell, G. A., Adams, L. G. The long-term culture of bovine monocyte-derived macrophages and their use in the study of intracellular proliferation of *Brucella abortus*. *Vet. Immunol. Immunopathol.* 34, 291–305 (1992)
9. Cellier, M., Govoni, G., Vidal, S., Kwan, T., Groulx, N., Liu, J., et al. Human natural resistance-associated macrophage protein: cDNA cloning, chromosomal mapping, genomic organization, and tissue-specific expression. *J. Exp. Med.* 180, 1741–1752 (1994).
10. Cerretti, D. P., Nelson, N., Kozlosky, C. J., Morrissey, P. J., Copeland, N. G., Gilbert, D. J., et al. The murine homolog of the human interleukin-8 receptor type B maps near the Ity/Lsh/Bcg disease resistance locus. *Genomics* 18, 410–413 (1993).
11. Chirgwin, J. M., Przybyla, A. E., MacDonald, R. J. Rutter, W. J. Isolation of biologically active ribonucleic acid from sources enriched in ribonuclease. *Biochemistry* 18, 5294–5299 (1979).
12. de Chastellier, C., Frehel, C., Offredo, C. Skamene, E. Implication of phagosomelysosome fusion in restriction of *Mycobacterium avium* growth in bone marrow macrophages from genetically resistant mice. *Infect. Immun.* 61, 3775–3784 (1993).

13. Dietrich, R. A., S. H. Hughes, and P. W. Gregory Economic and Epidemiologic Analysis of U.S. Bovine Brucellosis Programs. Primary Report, Vol. I, p. 1–24. Texas A&M University, College Station, Texas (1986).
14. Dosik, J. K., Barton, C. H., Holiday, D. L., Krall, M. M., Blackwell, J. M., Mock, B. A. An Nramp-related sequence maps to mouse Chromosome 17. *Mamm. Gen.* 5,458–460 (1994).
15. el-Gazzar, F. E. and E. H. MarthSalmonellae, salmonellosis, and dairy foods: a review. *J. Dairy Sci.* 75:2327–43 (1992).
16. Essey M. A. Bovine tuberculosis eradication: A national challenge, p.38–46. In B. Osburn (Ed.), *Proc. of the 12th Annual World Assoc. of Vet. Microbiologists, Immunologists, and Specialists in Infectious Diseases.* University of California, Davis Calif. (1991).
17. Essey, M. A. and M. A. Koller Status of bovine tuberculosis in North America. *Vet. Microbiol.* 40:15–22 (1994).
18. Feinberg, A. P., Vogelstein, B. A technique for radiolabeling DNA restriction endonuclease fragments to high specific activity. *Anal. Biochem.* 132, 6–13 (1983).
19. Frelier, P. F., Templeton, J. W., Estes, M., Whitford, H. W., Kienle, R. D. Genetic regulation of *Mycobacterium paratuberculosis* infection in recombinant inbred mice. *Vet. Pathol.* 17, 362–364 (1990).
20. Fries, R., Eggen, A., Womack, J. E. The bovine genome mapping project. *Mamm. Gen.* 4, 405–428 (1993)
21. Goto, Y. Buschman, E., Skamene, E. Regulation of host resistance to *Mycobacterium intracellular* in vivo and in vitro by Bcg gene. *Immunogenetics* 30, 218–221 (1989).
22. Gros, P., Skamene, E., Forget, A. Cellular mechanisms of genetically controlled host resistance to *Mycobacterium bovis* (BCG). *J. Immunol.* 131, 1966–1972 (1983).
23. Gruenheid, S., Cellier, M., Vidal, S., Gros, P. Identification and characterization of a second mouse Nramp gene. *Genomics* 25, 99–107 (1995).
24. Harmon, B. G., Templeton, J. W., Crawford, R. P., Williams, J. D., Adams, L. G. in *Genetic Control of Host Resistance to Infection and Malignancy.* (ed Skamene, E.) 345–354 (Alan R. Liss, Inc., New York, 1985).
25. Harmon, B. G., Adams, L. G., Templeton, J. W., Smith, R., III. Macrophage function in mammary glands of *Brucella abortus*-infected cows and cows that resisted infection after inoculation of *Brucella abortus. Am J. Vet. Res.* 50,459–465 (1989).
26. Ivanyi, J. Molecular biology of natural disease resistance-associated macrophage protein. *Parasitol. Today* 10,416–417 (1994).
27. Kramnik, I., Radzioch, D., Skamene, E. T-helper 1-like subset selection in *Mycobacterium bovis* bacillus Calmette-Guerin-infected resistant and susceptible mice. *Immunology* 81, 618–625 (1994).
28. Lim, W. A., Richards, F. M. Critical residues in an SH3 domain from Sem-1 suggests a mechanism for proline-rich peptide recognition. *Nature Struct. Biol.* 1, 221–225 (1994).
29. Malo, D., Vidal, S. M., Hu, J., Skamene, E., Gros, P. High-resolution linkage map in the vicinity of the host resistance locus Bcg. *Genomics* 16, 655–663 (1993).
30. Malo, D., Skamene, E. Genetic control of host resistance to infection. *TIG*; 10, 365–371 (1994).
31. Malo, D., Vogan, K., Vidal, S., Hu, J., Cellier, M., Schurr, E., et al. Haplotype mapping and sequence analysis of the mouse Nramp gene predicts susceptibility to infection with intracellular parasites. *Genomics* 23, 51–61 (1994).
32. Martin, S. W., R. A. Dietrich, P. Genho, W. P. Heuschele, R. L. Jones, M. Koller, J. D. Lee, H. Campos, A. Robinson, and G. W. Williams, Livestock disease eradication: Evaluation of the cooperative state-federal bovine tuberculosis eradication program. P. 1–97. National Research Council, Washington, D.C. (1994).
33. Mock, B., Krall, M., Blackwell, J., O'Brien, A. D., Schurr, E., Gros, P., et al. A genetic map of mouse chromosome 1 near the Lsh-Ity-Bcg disease resistance locus. *Genomics* 7, 57–64 (1990).
34. Musacchio, A., Saraste, M., Wilmans, M. High-resolution crystal structures of tyrosine kinase SH3 domains complexed with proline-rich peptides. *Nature Struct. Biol.* 1, 546–551 (1994).
35. Nathan, C. Natural Resistance and Nitric Oxide. *Cell* 82:873–876(1995).
36. Nowak, R. M. and Paradiso, J. L. In Walker's mammals of the World, 4th Edition, The John's Hopkins University Press, Baltimore and London (1983).
37. Pierson, M. D. and Corlett, D. A. HACCP: Principles and Applications. AVI Van Nostrand Reinhold, New York, N.Y., 212 (1992).
38. Plant, J. E., Blackwell, J. M. O'Brien, A. D., Bradley, D. J., Glynn, A. A. Are the Lsh and Ity disease resistance genes at one locus on mouse chromosome 1. *Nature* 297, 510–511 (1982).
39. Price, R. E., Templeton, J. W., Smith, R., III, Adams, L. G. Ability of mononuclear phagocytes from cattle naturally resistant or susceptible to brucellosis to control in vitro intracellular survival of *Brucella abortus. Infect. Immun.* 58, 879–886(1990)
40. Qureshi, T., Templeton, J. W., and Adams, L. G. Intracellular survival of Brucella abortus, Mycobacterium bovis (BCG), *Salmonella dublin* and *Salmonella typhimurium* in macrophages from cattle genetically resistant to *Brucella abortus.* Veterinary Immunology and Immunopathology 50:55–66 (1996).
41. Radzioch, D, Hudson, T., Boule, M., Barrera, L., Urbance, J. W., Varesio, L., et al. Genetic resistance/susceptibility to mycobacteria: phenotypic expression in bone marrow derived macrophage lines. *J. Leukoc. Bio.* 50, 263–272 (1991).
42. Roach, T. I. A., Chatterjee, D., Blackwell, J. M. Induction of early-response genes KC and JE by mycobacterial lipoarabinomannans: Regulation of KC expression in murine macrophages by Lsh/ity/Bcg (Candidate Nramp). *Infect. Immun.* 62, 1176–1184 (1994).
43. Roach, T. I. A., Kiderlen, A. F., Blackwell, J. M. Role of inorganic nitrogen oxides and tumor necrosis factor alpha in killing *Leishmania donovani* amastigotes in gamma interferon-lipopolysaccharide-activated macrophages from $Lsh^S$ and $Lsh^r$ congenic mouse strains. *Infect. Immun.* 59, 3935–3944 (1991).
44. Sanger, F., Niclden, S., Coulson, A. R. DNA sequencing with chain termination inhibitors. *Proc. Natl. Acad. Sci. USA* 74, 5463–5467 (1977).
45. Schurr, E., Malo, D., Radzioch, D., Buschman, E., Morgan, K., Gros, P., et al. Genetic control of innate resistance to mycobacterial infections. *Immunol. Today* 12, A42–A45 (1991).
46. Skamene, E., Gros, P., Forget, A., Patel, P. J. Nesbitt, M. N. Regulation of resistance to leprosy by chromosome 1 locus in the mouse. *Immunogenetics* 19, 117–124 (1984).
47. Skow, L. C., Adkinson, L., Womack, J. E., Beamer, W.G., Taylor, B. A. Mapping of the mouse fibronectin gene (Fn-1) to chromosome 1: conservation of the Idh-1-Cryg-Fn-1 synteny group in mammals. *Genomics* 1, 283–286 (1987).

48. Templeton, J. W., Adams, L. G. in *Advances in Brucellosis Research*. (ed Adams, L. G.) 144–150 (Texas A&M University Press, College Station, 1990).
49. Templeton, J. W. and L. G. Adams Genetics of natural resistance to tuberculosis, p. 29–32. In F. Griffin and G. de Lisle (eds.), *Tuberculosis in Wildlife and Domestic Animals*. University of Otago, Dunnedin, New Zealand (1996).
50. Templeton, J. W., Estes, D. M., Price, R. E., Smith, R., III, Adams, L. G. Immunogenetics of natural resistance to bovine brucellosis. 4th World *Cong. Genetics Applied to Livestock Production* 396–399 (1990).
51. Templeton, J. W., Smith, R. III, Adams, L. G. Natural disease resistance in domestic animals. *J. Am. Vet. Med. Assoc.* 192, 1306–1315(1988).
52. Tietjen, M and D. Y. Fung, Salmonellae and food safety. Crit. Rev. Microbiol. 21:53–83 (1995).
53. Vanderzant, Carl (Chairman), Subcommittee on Microbiological Criteria, Committee on Food Production, Food and Nutrition Board, National Research Council, An Evaluation of the Role of Microbiological Criteria for Foods and Food Ingredients. National Academy Press, Washington, D.C. 436 (1985).
54. Vidal, S. M., Malo, D., Vogan, K., Skamene, E., Gros, P. Natural resistance to infection with intracellular parasites: isolation of a candidate for Bcg. *Cell* 73, 469–485 (1993).
55. White, J. K., Shaw, M. A., Barton, C. H., Cerretti, D. P., Williams, H., Mock, B. A., et al. Genetic and physical mapping 2q35 in the region of the NRAMP and IL8R genes: Identification of a polymorphic repeat in the exon 2 of NRAMP. Genomics 24, 295–302 (1994).
56. Womack, J. E. Chromosomal evolution from the perspective of the bovine gene map. *Anim. Biotech.* 5, 123–128 (1994).
57. Womack, J. E., Moll, Y. D. Gene map of the cow: conservation of linkage with mouse and man. *J. Hered.* 77, 2–7 (1986).
58. Yu, H. Chen, J. K., Feng, S., Dalgarno, D. C., Brauer, A. W., Schreiber, S. L. Structural basis for the binding of proline-rich peptides to SH3 domains. *Cell* 76, 933–945 (1994).

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed is:

1. A method of detecting polymorphisms in the genetic material of an artiodactyla animal being resistant to disease caused by intracellular parasites comprising:

utilizing analytical methods to identify sequences homologous to the polymorphism of SEQ ID NO: 11 wherein said polymorphism corresponds to resistance to disease caused by said intracellular parasites.

2. The method of claim 1 wherein said analytical method is sequence analysis.

3. The method of claim 1 wherein said analytical method is nucleic acid hybridization.

4. The method of claim 1 wherein said analytical method is PCR.

5. The method of claim 1 wherein said artiodactyla is an ungulate.

6. The method of claim 5 wherein said ungulate is a ruminant.

7. The method of claim 1 wherein said disease caused by intracellular parasites is selected from the group consisting of brucellosis, tuberculosis, paratuberculosis and salmonellosis.

8. A method of detecting polymorphisms in the genetic material of an artiodactyla animal being susceptible to disease caused by intracellular parasites comprising:

utilizing analytical methods to identify sequences homologous to the polymorphism from the group consisting of SEQ ID NO: 12, SEQ ID NO: 13, and SEQ ID NO: 14 wherein said polymorphism corresponds to susceptibility to disease caused by said intracellular parasites.

9. The method of claim 8 wherein said analytical method is sequence analysis.

10. The method of claim 8 wherein said analytical method is nucleic acid hybridization.

11. The method of claim 8 wherein said analytical method is PCR.

12. The method of claim 8 wherein said artiodactyla is an ungulate.

13. The method of claim 12 wherein said ungulate is a ruminant.

14. The method of claim 8 wherein said disease caused by intracellular parasites is selected from the group consisting of brucellosis, tuberculosis, paratuberculosis and salmonellosis.

15. A method of detecting polymorphisms in the genetic material of a bovine animal being resistant to disease caused by intracellular parasites comprising:

utilizing analytical methods to identify the polymorphism from the group consisting of SEQ ID NO: 11, SEQ ID NO: 15, and SEQ ID NO: 31 wherein said polymorphism corresponds to resistance to disease caused by said intracellular parasites.

16. The method of claim 15 wherein said analytical method is PCR.

17. The method of claim 15 wherein said analytical method is PCR and utilizes at least one primer comprising a sequence selected from the group consisting of the sequences of SEQ ID NO:1 and SEQ ID NO: 2.

18. The method of claim 17 wherein the PCR utilizes both SEQ ID NO: 1 and SEQ ID NO:2.

19. The method of claim 15 wherein said analytical method is restriction digestion analysis.

20. The method of claim 15 wherein said analytical method is sequence analysis.

21. The method of claim 15 wherein said analytical method is single stranded conformational analysis.

22. The method of claim 15 wherein said analytical method is single stranded conformational polymorphism.

23. The method of claim 15 wherein said disease caused by intracellular parasites is selected from the group consisting of brucellosis, tuberculosis, paratuberculosis and salmonellosis.

24. A method of detecting polymorphisms in the genetic material of a bovine animal being susceptible to disease caused by intracellular parasites comprising:

utilizing analytical methods to identify the polymorphism from the group consisting of SEQ ID NO: 12, SEQ ID NO: 13, SEQ ID NO: 14, SEQ ID NO: 32, and SEQ ID NO: 33 wherein said polymorphism corresponds to susceptibility to disease caused by said intracellular parasites.

25. The method of claim 24 wherein said analytical method is PCR.

26. The method of claim 24 wherein said analytical method is PCR and utilizes at least one primer comprising a sequence selected from the group consisting of the sequences of SEQ ID NO:1 and SEQ ID NO: 2.

27. The method of claim 26 wherein the PCR utilizes both SEQ ID NO: 1 and SEQ ID NO:2.

28. The method of claim 24 wherein said analytical method is restriction digestion analysis.

29. The method of claim 24 wherein said analytical method is sequence analysis.

30. The method of claim 24 wherein said analytical method is single stranded conformational analysis.

31. The method of claim 24 wherein said analytical method is single stranded conformational polymorphism.

32. The method of claim 24 wherein said disease caused by intracellular parasites is selected from the group consisting of brucellosis, tuberculosis, paratuberculosis and salmonellosis.

33. A method for predicting the likelihood of a bovine animal being susceptible to disease caused by intracellular parasites comprising:

analyzing said bovine animal's genetic material by PCR for the presence of the genetic sequence of Nramp1 wherein the PCR utilizes at least one primer comprising a sequence selected from the group consisting of the sequences of SEQ ID NO: 1 and SEQ ID NO: 2, the presence of said sequence of Nramp1 in situ being associated with susceptibility of said bovine animal to disease caused by intracellular parasites.

34. The method of claim 33 wherein the PCR utilizes both SEQ ID NO: 1 and SEQ ID NO: 2.

35. The method of claim 33 wherein said disease caused by intracellular parasites is selected from the group consisting of brucellosis, tuberculosis, paratuberculosis and salmonellosis.

36. A method for predicting the likelihood of a bovine animal being resistant to disease caused by intracellular parasites comprising:

analyzing said bovine animal's genetic material by PCR for the presence of the genetic sequence of Nramp1 wherein the PCR utilizes at least one primer comprising a sequence selected from the group consisting of the sequences of SEQ ID NO: 1 and SEQ ID NO: 2, the presence of said sequence of Nramp1 in situ being associated with resistance of said bovine animal to disease caused by intracellular parasites.

37. The method of claim 36 wherein the PCR utilizes both SEQ ID NO: 1 and SEQ ID NO:2.

38. The method of claim 36 wherein said disease caused by intracellular parasites is selected from the group consisting of brucellosis, tuberculosis, paratuberculosis and salmonellosis.

39. A method of predicting the likelihood of a bovine animal being resistant to disease caused by intracellular parasites by identifying polymorphisms in the genetic material of a bovine animal comprising:

amplification of nucleic acid sequences with PCR utilizing at least one primer comprising a sequence selected from the group consisting of the sequences of SEQ ID NO: 1 and SEQ ID NO: 2; and analyzing said amplified nucleic acid sequences, wherein said amplified nucleic acid sequences which contain a sequence from the group consisting of SEQ ID NO: 11, SEQ ID NO: 15, and SEQ ID NO: 31 correspond to a bovine animal resistant to said intracellular parasites.

40. The method of claim 39 wherein the PCR utilizes both SEQ ID NO: 1 and SEQ ID NO:2.

41. The method of claim 39 wherein said disease caused by intracellular parasites is selected from the group consisting of brucellosis, tuberculosis, paratuberculosis and salmonellosis.

42. A method of predicting the likelihood of a bovine animal being susceptible to disease caused by intracellular parasites by identifying polymorphisms in the genetic material of a bovine animal comprising:

amplification of nucleic acid sequences with PCR utilizing at least one primer comprising a sequence selected from the group consisting of the sequences of SEQ ID NO: 1 and SEQ ID NO: 2; and analyzing said amplified nucleic acid sequences, wherein said amplified nucleic acid sequences which contain a sequence from the group consisting of SEQ ID NO: 12, SEQ ID NO: 13, SEQ ID NO: 14, SEQ ID NO: 32 and SEQ ID NO: 33 corresponds to abovine animal susceptible to said intracellular parasites.

43. The method of claim 42 wherein the PCR utilizes both SEQ ID NO: 1 and SEQ ID NO:2.

44. The method of claim 42 wherein said disease caused by intracellular parasites is selected from the group consisting of brucellosis, tuberculosis, paratuberculosis and salmonellosis.

* * * * *

```
SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

AAGGCAGCAA GACAGACAGG                                              20

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

ATGGAACTCA CGTTGGCTG                                               19

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:
```

```
TCTCTGGCTG AAGGCTCTCC                                              20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

CCAAGCTCAC CTTAGGGTAG                                              20

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

CGTGGTGACA GGCAAGGAC                                               19

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS:    single
        (D) TOPOLOGY: linear (ii) MOLECULE TYPE: DNA (xi) SEQUENCE DESCRIPTION: SEQ ID NO:6:

CCAAGAAGAG GAAGAAGAAG GTGTC                                        25

(2) INFORMATION FOR SEQ ID NO:7:

(i) SEQUENCE CHARACTERISTICS:
        (A) LENGTH: 547 amino acids
        (B) TYPE: amino acids
        (D) TOPOLOGY: linear (ii) MOLECULE TYPE: peptide (xi) SEQUENCE DESCRIPTION: SEQ ID NO:7:

Met  Thr  Gly  Asp  Lys  Gly  Pro  Gln  Arg  Leu  Ser  Gly
                    5                        10

Ser  Ser  Tyr  Gly  Ser  Ile  Ser  Ser  Pro  Thr  Ser  Pro
          15                       20

Gly  Pro  Gln  Gln  Ala  Pro  Pro  Arg  Glu  Thr  Tyr  Leu
25                       30                       35

Ser  Glu  Lys  Ile  Pro  Ile  Pro  Asp  Thr  Lys  Pro  Gly
               40                   45

Thr  Phe  Ser  Leu  Arg  Lys  Leu  Trp  Ala  Phe  Thr  Gly
     50                   55                           60

Pro  Gly  Phe  Leu  Met  Ser  Ile  Ala  Phe  Leu  Asp  Pro
                    65                   70

Gly  Asn  Ile  Glu  Ser  Asp  Leu  Gln  Ala  Gly  Ala  Val
```

```
                    75                          80
Ala  Gly  Phe  Lys  Leu  Leu  Trp  Val  Leu  Leu  Trp  Ala
 85                      90                          95

Thr  Val  Leu  Gly  Leu  Leu  Cys  Gln  Arg  Leu  Ala  Ala
               100                 105

Arg  Leu  Gly  Val  Val  Thr  Gly  Lys  Asp  Leu  Gly  Glu
     110                      115                     120

Val  Cys  His  Cys  Tyr  Tyr  Pro  Lys  Val  Pro  Arg  Thr
                    125                      130

Val  Leu  Trp  Leu  Thr  Ile  Glu  Leu  Ala  Ile  Val  Gly
          135                      140

Ser  Asp  Met  Gln  Glu  Val  Ile  Gly  Thr  Ala  Ile  Ala
145                           150                155

Phe  Asn  Leu  Leu  Ser  Ala  Gly  Arg  Ile  Pro  Leu  Trp
               160                 165

Gly  Gly  Val  Leu  Ile  Thr  Ile  Val  Asp  Thr  Phe  Phe
     170                      175                     180

Phe  Leu  Phe  Leu  Asp  Asn  Tyr  Gly  Leu  Arg  Lys  Leu
               185                      190

Glu  Ala  Phe  Phe  Gly  Leu  Leu  Ile  Thr  Ile  Met  Ala
          195                      200

Leu  Thr  Phe  Gly  Tyr  Glu  Tyr  Val  Val  Ala  Arg  Pro
205                      210                     215

Glu  Gln  Gly  Ala  Leu  Leu  Arg  Gly  Leu  Phe  Leu  Pro
               220                 225

Ser  Cys  Pro  Gly  Cys  Gly  His  Pro  Glu  Leu  Leu  Gln
     230                      235                     240

Ala  Val  Gly  Ile  Val  Gly  Ala  Ile  Ile  Met  Pro  His
               245                      250

Asn  Ile  Tyr  Leu  His  Ser  Ala  Leu  Val  Lys  Ser  Arg
          255                      260

Glu  Ile  Asp  Arg  Ala  Arg  Arg  Ala  Asp  Ile  Arg  Glu
265                      270                     275

Ala  Asn  Met  Tyr  Phe  Leu  Ile  Glu  Ala  Thr  Ile  Ala
               280                      285

Leu  Ser  Val  Ser  Phe  Ile  Ile  Asn  Leu  Phe  Val  Met
     290                      295                     300

Ala  Val  Phe  Gly  Gln  Ala  Phe  Tyr  Gln  Lys  Thr  Asn
               305                      310

Gln  Ala  Ala  Phe  Asn  Ile  Cys  Ala  Asn  Ser  Ser  Leu
               315                      320

His  Asp  Tyr  Ala  Lys  Ile  Phe  Pro  Met  Asn  Asn  Ala
325                      330                     335

Thr  Val  Ala  Val  Asp  Ile  Tyr  Gln  Gly  Gly  Val  Ile
               340                      345

Leu  Gly  Cys  Leu  Phe  Gly  Pro  Ala  Ala  Leu  Tyr  Ile
     350                      355                     360

Trp  Ala  Ile  Gly  Leu  Leu  Ala  Ala  Gly  Gln  Ser  Ser
               365                      370

Thr  Met  Thr  Gly  Thr  Tyr  Ala  Gly  Gln  Phe  Val  Met
          375                      380

Glu  Gly  Phe  Leu  Arg  Leu  Arg  Trp  Ser  Arg  Phe  Ala
385                      390                     395
```

```
Arg  Val  Leu  Leu  Thr  Arg  Ser  Cys  Ala  Ile  Leu  Pro
               400                     405

Thr  Val  Leu  Val  Ala  Val  Phe  Arg  Asp  Leu  Arg  Asp
          410                 415                      420

Leu  Ser  Gly  Leu  Asn  Asp  Leu  Leu  Asn  Val  Leu  Gln
                    425                 430

Ser  Leu  Leu  Leu  Pro  Phe  Ala  Val  Leu  Pro  Ile  Leu
               435                 440

Thr  Phe  Thr  Ser  Met  Pro  Thr  Leu  Met  Gln  Glu  Phe
445                      450                      455

Ala  Asn  Gly  Leu  Leu  Asn  Lys  Val  Val  Thr  Ser  Ser
               460                 465

Ile  Met  Val  Leu  Val  Cys  Ala  Ile  Asn  Leu  Tyr  Phe
          470                 475                      480

Val  Val  Ser  Tyr  Leu  Pro  Ser  Leu  Pro  His  Pro  Ala
                    485                      490

Tyr  Phe  Gly  Leu  Ala  Ala  Leu  Leu  Ala  Ala  Ala  Tyr
               495                      500

Leu  Gly  Leu  Ser  Thr  Tyr  Leu  Val  Trp  Thr  Cys  Cys
505                      510                      515

Leu  Ala  His  Gly  Ala  Thr  Pro  Leu  Ala  His  Ser  Ser
               520                      525

His  His  His  Phe  Leu  Tyr  Gly  Leu  Leu  Glu  Glu  Asp
          530                      535                 540

Gln  Lys  Gly  Glu  Thr  Ser  Gly
                    545
```

(2) INFORMATION FOR SEQ ID NO:8:

(i) SEQUENCE CHARACTERISTICS:
        (A) LENGTH: 548 amino acids
        (B) TYPE: amino acid
        (D) TOPOLOGY: linear (ii) MOLECULE TYPE: peptide (xi) SEQUENCE DESCRIPTION: SEQ ID NO:8:

```
Met  Ile  Ser  Asp  Lys  Ser  Pro  Pro  Arg  Leu  Ser  Arg
               5                        10

Pro  Ser  Tyr  Gly  Ser  Ile  Ser  Ser  Leu  Pro  Gly  Pro
          15                  20

Ala  Pro  Gln  Pro  Ala  Pro  Cys  Arg  Glu  Thr  Tyr  Leu
25                  30                       35

Ser  Glu  Lys  Ile  Pro  Ile  Pro  Ser  Ala  Asp  Gln  Gly
               40                  45

Thr  Phe  Ser  Leu  Arg  Lys  Leu  Trp  Ala  Phe  Thr  Gly
     50                  55                           60

Pro  Gly  Phe  Leu  Met  Ser  Ile  Ala  Phe  Leu  Asp  Pro
                    65                  70

Gly  Asn  Ile  Glu  Ser  Asp  Leu  Gln  Ala  Gly  Ala  Val
          75                  80

Ala  Gly  Phe  Lys  Leu  Leu  Trp  Val  Leu  Leu  Trp  Ala
85                  90                            95

Thr  Val  Leu  Gly  Leu  Leu  Cys  Gln  Arg  Leu  Ala  Ala
               100                 105
```

```
Arg  Leu  Gly  Val  Val  Thr  Gly  Lys  Asp  Leu  Gly  Glu
     110            115                           120

Val  Cys  His  Leu  Tyr  Tyr  Pro  Lys  Val  Pro  Arg  Ile
                    125                 130

Leu  Leu  Trp  Leu  Thr  Ile  Glu  Leu  Ala  Ile  Val  Gly
               135                 140

Ser  Asp  Met  Gln  Glu  Val  Ile  Gly  Thr  Ala  Ile  Ser
145                      150                      155

Phe  Asn  Leu  Leu  Ser  Ala  Gly  Arg  Ile  Pro  Leu  Trp
               160                 165

Gly  Gly  Val  Leu  Ile  Thr  Ile  Val  Asp  Thr  Phe  Phe
     170                 175                      180

Phe  Leu  Phe  Leu  Asp  Asn  Tyr  Gly  Leu  Arg  Lys  Leu
                    185                      190

Glu  Ala  Phe  Phe  Gly  Leu  Leu  Ile  Thr  Ile  Met  Ala
               195                 200

Leu  Thr  Phe  Gly  Tyr  Glu  Tyr  Val  Val  Ala  His  Pro
205                      210                      215

Ser  Gln  Gly  Ala  Leu  Leu  Lys  Gly  Leu  Val  Leu  Pro
               220                 225

Thr  Cys  Pro  Gly  Cys  Gly  Gln  Pro  Glu  Leu  Leu  Gln
     230                 235                           240

Ala  Val  Gly  Ile  Val  Gly  Ala  Ile  Ile  Met  Pro  His
                    245                 250

Asn  Ile  Tyr  Leu  His  Ser  Ala  Leu  Val  Lys  Ser  Arg
               255                 260

Glu  Val  Asp  Arg  Thr  Arg  Arg  Val  Asp  Val  Arg  Glu
265                      270                      275

Ala  Asn  Met  Tyr  Phe  Leu  Ile  Glu  Ala  Thr  Ile  Ala
               280                 285

Leu  Ser  Val  Ser  Phe  Ile  Ile  Asn  Leu  Phe  Val  Met
     290                 295                           300

Ala  Val  Phe  Gly  Gln  Ala  Phe  Tyr  Gln  Gln  Thr  Asn
                    305                 310

Glu  Glu  Ala  Phe  Asn  Ile  Cys  Ala  Asn  Ser  Ser  Leu
               315                 320

Gln  Asn  Tyr  Ala  Lys  Ile  Phe  Pro  Arg  Asp  Asn  Asn
325                      330                      335

Thr  Val  Ser  Val  Asp  Ile  Tyr  Gln  Gly  Gly  Val  Ile
               340                 345

Leu  Gly  Cys  Leu  Phe  Gly  Pro  Ala  Ala  Leu  Tyr  Ile
     350                 355                           360

Trp  Ala  Val  Gly  Leu  Leu  Ala  Ala  Gly  Gln  Ser  Ser
                    365                 370

Thr  Met  Thr  Gly  Thr  Tyr  Ala  Gly  Gln  Phe  Val  Met
               375                 380

Glu  Gly  Phe  Leu  Lys  Leu  Arg  Trp  Ser  Arg  Phe  Ala
385                      390                      395

Arg  Val  Leu  Leu  Thr  Arg  Ser  Cys  Ala  Ile  Leu  Pro
               400                 405

Thr  Val  Leu  Val  Ala  Val  Phe  Arg  Asp  Leu  Lys  Asp
     410                 415                           420

Leu  Ser  Gly  Leu  Asn  Asp  Leu  Leu  Asn  Val  Leu  Gln
```

-continued

```
                         425                           430
Ser  Leu  Leu  Leu  Pro  Phe  Ala  Val  Leu  Pro  Ile  Leu
          435                      440

Thr  Phe  Thr  Ser  Met  Pro  Ala  Val  Met  Gln  Glu  Phe
445                      450                     455

Ala  Asn  Gly  Arg  Met  Ser  Lys  Ala  Ile  Thr  Ser  Cys
               460                     465

Ile  Met  Ala  Leu  Val  Cys  Ala  Ile  Asn  Leu  Tyr  Phe
     470                     475                          480

Val  Ile  Ser  Tyr  Leu  Pro  Ser  Leu  Pro  His  Pro  Ala
                    485                          490

Tyr  Phe  Gly  Leu  Val  Ala  Leu  Phe  Ala  Ile  Gly  Tyr
          495                          500

Leu  Gly  Leu  Thr  Ala  Tyr  Leu  Ala  Trp  Thr  Cys  Cys
505                           510                    515

Ile  Ala  His  Gly  Ala  Thr  Phe  Leu  Thr  His  Ser  Ser
               520                     525

His  Lys  His  Phe  Leu  Tyr  Gly  Leu  Pro  Asn  Glu  Glu
530                           535                         540

Gln  Gly  Gly  Val  Gln  Gly  Ser  Gly
                    545
```

(2) INFORMATION FOR SEQ ID NO:9:

(i) SEQUENCE CHARACTERISTICS:
        (A) LENGTH: 548 amino acids
        (B) TYPE: amino acid
        (D) TOPOLOGY: linear (ii) MOLECULE TYPE: peptide (xi) SEQUENCE DESCRIPTION: SEQ ID NO:9:

```
Met  Ser  Gly  Asp  Thr  Gly  Pro  Pro  Lys  Gln  Gly  Gly
               5                         10

Thr  Arg  Tyr  Gly  Ser  Ile  Ser  Ser  Pro  Pro  Ser  Pro
          15                      20

Glu  Pro  Gln  Gln  Ala  Pro  Pro  Gly  Gly  Thr  Tyr  Leu
25                       30                      35

Ser  Glu  Lys  Ile  Pro  Ile  Pro  Asp  Thr  Glu  Ser  Gly
               40                      45

Thr  Phe  Ser  Leu  Arg  Lys  Leu  Trp  Ala  Phe  Thr  Gly
     50                      55                           60

Pro  Gly  Phe  Leu  Met  Ser  Ile  Ala  Phe  Leu  Asp  Pro
                    65                      70

Gly  Asn  Ile  Glu  Ser  Asp  Leu  Gln  Ala  Gly  Ala  Val
          75                      80

Ala  Gly  Phe  Lys  Leu  Leu  Trp  Val  Leu  Leu  Trp  Ala
85                       90                           95

Thr  Val  Leu  Gly  Leu  Leu  Cys  Gln  Arg  Leu  Ala  Ala
               100                     105

Arg  Leu  Gly  Val  Val  Thr  Gly  Lys  Asp  Leu  Gly  Glu
     110                     115                          120

Val  Cys  His  Leu  Tyr  Tyr  Pro  Lys  Val  Pro  Arg  Ile
                    125                          130

Leu  Leu  Trp  Leu  Thr  Ile  Glu  Leu  Ala  Ile  Val  Gly
               135                     140
```

```
Ser  Asp  Met  Gln  Glu  Val  Ile  Gly  Thr  Ala  Ile  Ala
145                 150                      155

Phe  Ser  Leu  Leu  Ser  Ala  Gly  Arg  Ile  Pro  Leu  Trp
               160                 165

Gly  Gly  Val  Leu  Ile  Thr  Val  Val  Asp  Thr  Phe  Phe
          170            175                      180

Phe  Leu  Phe  Leu  Asp  Asn  Tyr  Gly  Leu  Arg  Lys  Leu
                    185                      190

Glu  Ala  Phe  Phe  Gly  Phe  Leu  Ile  Thr  Ile  Met  Ala
               195                 200

Leu  Thr  Phe  Gly  Tyr  Glu  Tyr  Val  Val  Ala  Gln  Pro
205                      210                 215

Ala  Gln  Gly  Ala  Leu  Leu  Gln  Gly  Leu  Phe  Leu  Pro
               220                 225

Ser  Cys  Pro  Gly  Cys  Gly  Gln  Pro  Glu  Leu  Leu  Gln
     230                      235                      240

Ala  Val  Gly  Ile  Ile  Gly  Ala  Ile  Ile  Met  Pro  His
               245                      250

Asn  Ile  Tyr  Leu  His  Ser  Ser  Leu  Val  Lys  Ser  Arg
          255                 260

Glu  Val  Asp  Arg  Ser  Arg  Arg  Ala  Asp  Ile  Arg  Glu
265                 270                      275

Ala  Asn  Met  Tyr  Phe  Leu  Ile  Glu  Ala  Thr  Ile  Ala
               280                 285

Leu  Ser  Val  Ser  Phe  Leu  Ile  Asn  Leu  Phe  Val  Met
     290                 295                           300

Ala  Val  Phe  Gly  Gln  Ala  Phe  Tyr  Lys  Gln  Thr  Asn
               305                      310

Gln  Ala  Ala  Phe  Asn  Ile  Cys  Ala  Asp  Ser  Ser  Leu
          315                 320

His  Asp  Tyr  Ala  Pro  Ile  Phe  Pro  Arg  Asn  Asn  Leu
325                 330                      335

Thr  Val  Ala  Val  Asp  Ile  Tyr  Gln  Gly  Gly  Val  Ile
               340                 345

Leu  Gly  Cys  Leu  Phe  Gly  Pro  Pro  Ala  Leu  Tyr  Ile
350                      355                      360

Trp  Ala  Val  Gly  Leu  Leu  Ala  Ala  Gly  Gln  Ser  Ser
               365                      370

Thr  Met  Thr  Gly  Thr  Tyr  Ala  Gly  Gln  Phe  Val  Met
          375                      380

Glu  Gly  Phe  Leu  Lys  Leu  Arg  Trp  Ser  Arg  Phe  Ala
385                      390                 395

Arg  Val  Leu  Leu  Thr  Arg  Ser  Cys  Ala  Ile  Leu  Pro
               400                 405

Thr  Val  Leu  Leu  Ala  Val  Phe  Arg  Asp  Leu  Arg  Asp
          410                 415                      420

Leu  Ser  Gly  Leu  Asn  Asp  Leu  Leu  Asn  Val  Leu  Gln
                    425                 430

Ser  Leu  Leu  Leu  Pro  Phe  Ala  Val  Leu  Pro  Ile  Leu
          435                 440

Thr  Phe  Thr  Ser  Met  Pro  Ala  Leu  Met  Gln  Glu  Phe
445                      450                      455
```

| Ala | Asn | Gly | Leu | Val | Ser | Lys | Val | Ile | Thr | Ser | Ser |
|---|---|---|---|---|---|---|---|---|---|---|---|
| | | | 460 | | | | | 465 | | | |

| Ile | Met | Val | Leu | Val | Cys | Ala | Val | Asn | Leu | Tyr | Phe |
|---|---|---|---|---|---|---|---|---|---|---|---|
| | 470 | | | | | 475 | | | | | 480 |

| Val | Ile | Ser | Tyr | Leu | Pro | Ser | Leu | Pro | His | Pro | Ala |
|---|---|---|---|---|---|---|---|---|---|---|---|
| | | | | 485 | | | | | 490 | | |

| Tyr | Phe | Ser | Leu | Val | Ala | Leu | Leu | Ala | Ala | Ala | Tyr |
|---|---|---|---|---|---|---|---|---|---|---|---|
| | | 495 | | | | | 500 | | | | |

| Leu | Gly | Leu | Thr | Thr | Tyr | Leu | Val | Trp | Thr | Cys | Leu |
|---|---|---|---|---|---|---|---|---|---|---|---|
| 505 | | | | | 510 | | | | | 515 | |

| Ile | Thr | Gln | Gly | Ala | Thr | Leu | Leu | Ala | His | Ser | Ser |
|---|---|---|---|---|---|---|---|---|---|---|---|
| | | | 520 | | | | | 525 | | | |

| His | Gln | Arg | Phe | Leu | Tyr | Gly | Leu | Pro | Glu | Glu | Asp |
|---|---|---|---|---|---|---|---|---|---|---|---|
| | 530 | | | | | 535 | | | | | 540 |

| Gln | Glu | Lys | Gly | Arg | Thr | Ser | Gly |
|---|---|---|---|---|---|---|---|
| | | | | 545 | | | |

(2) INFORMATION FOR SEQ ID NO:10:

(i) SEQUENCE CHARACTERISTICS:
        (A) LENGTH: 2271 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
GCTTGCCATG CCCGTGAGGG GCTGCCCGGC ACGCCAGCCA CTCGCACAGA           50

GAGTGCCCGA GCCTGCGGTC CTCATGTCAG GTGACACGGG CCCCCCAAAG          100

CAGGGAGGGA CCAGATATGG CTCCATCTCC AGCCCACCCA GTCCAGAGCC          150

ACAGCAAGCA CCTCCCGGAG GGACCTACCT AAGTGAGAAG ATCCCCATTC          200

CGGATACAGA ATCGGGTACA TTCAGCCTGA GGAAGCTGTG GGCCTTCACG          250

GGGCCTGGAT TCCTCATGAG CATCGCATTC CTGGACCCAG AAACATTGA           300

GTCGGATCTT CAGGCTGGGG CTGTGGCTGG ATTCAAACTG CTCTGGGTGC          350

TGCTGTGGGC CACAGTGTTG GGCTTGCTTT GCCAGCGACT GGCTGCCCGG          400

CTGGGCGTGG TGACAGGCAA GGACTTGGGC GAGGTCTGCC ATCTCTACTA          450

CCCTAAGGTG CCCCGCATTC TCCTCTGGCT GACCATCGAG CTAGCCATCG          500

TGGGCTCAGA CATGCAGGAA GTCATTGGCA CAGCTATTGC ATTCAGTCTG          550

CTCTCCGCCG GACGAATCCC ACTCTGGGGT GGTGTCCTCA TCACCGTCGT          600

GGACACTTTC TTCTTCCTCT TCCTCGATAA CTACGGGTTG CGGAAGCTGG          650

AAGCCTTTTT TGGATTTCTT ATTACCATAA TGGCCTTGAC CTTCGGCTAT          700

GAGTACGTGG TGGCTCAGCC TGCTCAGGGA GCATTGCTTC AGGGCCTGTT          750

CCTGCCCTCG TGCCCAGGCT GTGGCCAGCC CGAGCTGCTG CAAGCCGTGG          800

GCATCATTGG CGCCATCATC ATGCCCCACA ACATCTACCT GCATTCCTCC          850

CTGGTCAAGT CTCGAGAGGT AGACCGGTCC CGGCGGGCGG ACATCCGAGA          900

GGCCAACATG TACTTCCTGA TTGAAGCCAC CATCGCCCTG TCTGTCTCCT          950

TCCTCATCAA CCTGTTTGTC ATGGCTGTCT TTGGGCAAGC CTTCTACAAG         1000

CAAACCAACC AGGCTGCGTT CAACATCTGT GCCGACAGCA GCCTCCACGA         1050
```

```
CTACGCGCCG ATCTTTCCCA GGAACAACCT GACCGTGGCA GTGGACATTT      1100

ACCAAGGAGG CGTGATCCTG GGCTGCCTCT TTGGTCCTCC AGCCCTGTAC      1150

ATCTGGGCCG TGGGTCTCCT GGCTGCTGGG CAGAGCTCCA CCATGACCGG      1200

CACCTACGCG GGACAGTTTG TGATGGAGGG CTTCCTGAAG CTGCGGTGGT      1250

CACGCTTCGC CCGAGTCCTG CTCACTCGCT CCTGCGCCAT CCTGCCCACT      1300

GTGCTCCTGG CTGTCTTCAG GGACTTGCGG GACCTGTCAG GCCTCAACGA      1350

CCTGCTCAAT GTGCTGCAGA GCCTGCTGCT TCCCTTCGCT GTGCTGCCCA      1400

TCCTCACCTT CACCAGCATG CCCGCCCTGA TGCAGGAGTT TGCCAATGGC      1450

CTGGTGAGCA AAGTTATCAC TTCCTCCATC ATGGTGCTGG TCTGCGCCGT      1500

CAACCTTTAC TTCGTGATCA GCTACTTGCC CAGCCTCCCC CACCCTGCCT      1550

ACTTCAGCCT TGTAGCACTG CTGGCCGCAG CCTACCTGGG CCTCACCACT      1600

TACCTGGTCT GGACCTGTCT CATCACCCAG GGAGCCACTC TTCTGGCCCA      1650

CAGTTCCCAC CAACGCTTCC TGTATGGGCT TCCTGAAGAG GATCAGGAGA      1700

AGGGGAGGAC CTCGGGATGA GCTCCCACCA GGGCCTGGCC ACGGGTGGAA      1750

TGAGTGGGCA CAGTGGCCTG TCAGACAAGG GTGTGTGTGT GTGTGTGTGT      1800

GTGTATGTGT GTGAAGGCAG CAAGACAGAC AGGGAGTTCT GGAAGCTGGC      1850

CAACGTGAGT TCCAGAGGGA CCTGTGTGTG TGTGACACAC TGGCCTGCCA      1900

GACAAGGGTG TGTGTGTGTG TGTGTGTGTG TGTGCATGCA CAGCAAGACG      1950

GAGAGGGAGT TCTGGAAGGC AGCCAACGTG AGTTCCATAG GGACCTGCTA      2000

TTTCCTAGCT CAGATCTCAG TGTTCTTGAC TATAAAATGG GGACACCTAC      2050

CTTGGAGTGG TTGTAAATAA GACACTTGAA CGCAGAGCCT AGCACTTCAG      2100

ATTTAAAAAC AAAAGAATCA TAATTCCAAA AGTTACTGAG CACTATCACA      2150

GGAGTGACCT GACAGACCCA CCCAGTCTAG GGTGGGACCC AGGCTCCAAA      2200

CTGATTTAAA ATAAGAGTCT GAAAATGCTA AATAAATGCT GTTGTGCTTA      2250

GTCCCCGAGA AAAAAAAAA A                                     2271
```

(2) INFORMATION FOR SEQ ID NO:11:

(i) SEQUENCE CHARACTERISTICS:
        (A) LENGTH: 155 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

```
GGGTGTGTGT GTGTGTGTGT GTGTGTATGT GTGTGAAGGC AGCAAGACAG       50

ACAGGGAGTT CTGGAAGCTG GCCAACGTGA GTTCCAGAGG GACCTGTGTG      100

TGTGTGACAC ACTGGCCTGC CAGACAAGGG TGTGTGTGTG TGTGTGTGTG      150

TGTGT                                                      155
```

(2) INFORMATION FOR SEQ ID NO:12:

(i) SEQUENCE CHARACTERISTICS:
        (A) LENGTH: 155 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GGGGGTGTGT GTGTGTGTGT ATGTGTGTGA AGGCAGCAAG ACAGACAGGG        50

AGTTCTGGAA GCTGGCCAAC GTGAGTTCCA GAGGGACCTG TGTGTGTGTG       100

ACACACTGGC CTGCCAGACA AGGGTGTGTG TGTGTGTGTG TGTGTGTGTG       150

TGTGT                                                        155

(2) INFORMATION FOR SEQ ID NO:13:

(i) SEQUENCE CHARACTERISTICS:
            (A) LENGTH: 155 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:13:

GGGGGTGTGT GTGTGTGTGT GTATGTGTGT GAAGGCAGCA AGACAGACAG        50

GGAGTTCTGG AAGCTGGCCA ACGTGAGTTC CAGAGGGACC TGTGTGTGTG       100

TGACACACTG GCCTGCCAGA CAAGGGTGTG TGTGTGTGTG TGTGTGTGTG       150

TGTGT                                                        155

(2) INFORMATION FOR SEQ ID NO:14:

(i) SEQUENCE CHARACTERISTICS:
            (A) LENGTH: 155 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:14:

GGGGGTGTGT GTGTGTGTGT GTGTATGTGT GTGAAGGCAG CAAGACAGAC        50

AGGGAGTTCT GGAAGCTGGC CAACGTGAGT TCCAGAGGGA CCTGTGTGTG       100

TGTGACACAC TGGCCTGCCA GACAAGGGTG TGTGTGTGTG TGTGTGTGTG       150

TGTGT                                                        155

(2) INFORMATION FOR SEQ ID NO:15:

(i) SEQUENCE CHARACTERISTICS:
            (A) LENGTH: 155 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:15:

GGGTGTGTGT GTGTGTGTGT GTGTGTATGT GTGTNNNNNN NNNNNNNNNN        50

NNNNNNNNNN NNNNNNNNNN NNNNNNNNNN NNNNNNNNNN NNNNNGTGTG       100

TGTGTNNNNN NNNNNNNNNN NNNNNNNNNG TGTGTGTGTG TGTGTGTGTG       150

TGTGT                                                        155

(2) INFORMATION FOR SEQ ID NO:16:

(i) SEQUENCE CHARACTERISTICS:
            (A) LENGTH: 449 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:16:

| | | | | | |
|---|---|---|---|---|---|
| TCCCACCAAC | GCTTCCTGTA | TGGGCTTCCT | GAAGAGGATC | AGGAGAAGGG | 50 |
| GAGGACCTCG | GGATGAGCTC | CCACCAGGGC | CTGGCCACGG | GTGGAATGAG | 100 |
| TGGGCACAGT | GGCCTGTCAG | ACAAGGGTGT | GTGTGTGTGT | GTGTGTGTGT | 150 |
| ATGTGTGTGA | AGGCAGCAAG | ACAGACAGGG | AGTTCTGGAA | GCTGGCCAAC | 200 |
| GTGAGTTCCA | GAGGGACCTG | TGTGTGTGTG | ACACACTGGC | CTGCCAGACA | 250 |
| AGGGTGTGTG | TGTGTGTGTG | TGTGTGTGTG | CATGCACAGC | AAGACGGAGA | 300 |
| GGGAGTTCTG | GAAGGCAGCC | AACGTGAGTT | CCATAGGGAC | CTGCTATTTC | 350 |
| CTAGCTCAGA | TCTCAGTGTT | CTTGACTATA | AATGGGGAC | ACCTACCTTG | 400 |
| GAGTGGTTGT | AAATAAGACA | CTTGAACGCA | GAGCCTAGCA | CTTCAGATT | 449 |

(2) INFORMATION FOR SEQ ID NO:17:

(i) SEQUENCE CHARACTERISTICS:
            (A) LENGTH: 443 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:17:

| | | | | | |
|---|---|---|---|---|---|
| TCCCACCAAC | GCTTCCTGTA | TGGGCTTCCT | GAAGAGGATC | AGGAGAAGGG | 50 |
| GAGGACCTCG | GGATGAGCTC | CCACCAGGGC | CTGGCCACGG | GTGGAATGAG | 100 |
| TGGGCACAGT | GGCCTGTCAG | ACAAGGGTGT | GTGTGTGTGT | GTGTGTGTGT | 150 |
| GTGAAGGCAG | CAAGACAGAC | AGGGAGTTCT | GGAAGCTGGC | CAACGTGAGT | 200 |
| TCCAGAGGGA | CCTGTGTGTG | TGTGTGTGTC | TGGCCTGCCA | GACAAGGGTG | 250 |
| TGTGTGTGTG | TGTGTGTGTG | TGTGTGTGTA | CAGCAAGACG | GAGAGGGAGT | 300 |
| TCTGGAAGGC | AGCCAACGTG | AGTTCCATAG | GGACCTGCTA | TTTCCTAGCT | 350 |
| CAGATCTCAG | TGTTCTTGAC | TATAAAATGG | GGACACCTAC | CTTGGAGTGG | 400 |
| TTGTAAATAA | GACACTTGAA | CGCAGAGCCT | AGCACTTCAG | ATT | 443 |

(2) INFORMATION FOR SEQ ID NO:18:

(i) SEQUENCE CHARACTERISTICS:
            (A) LENGTH: 445 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:18:

| | | | | | |
|---|---|---|---|---|---|
| TCCCACCAAC | GCTTCCTGTA | TGGGCTTCCT | GAAGAGGATC | AGGAGAAGGG | 50 |
| GAGGACCTCG | GGATGAGCTC | CCACCAGGGC | CTGGCCACGG | GTGGGATGAG | 100 |
| TGGGCACAGT | GGCCTGTCAG | ACAAAGGGGT | GTGTGTGTGT | GTGTGTGTAT | 150 |
| GTGTGCGAAG | GCAGCAAGAC | AGACAGGGAG | TTCTGGAAGC | TGGCCAACGT | 200 |

```
GAGTTCCAGA GGGACCTGTG TGTGTGTGAC ACACTGGCCT GCCAGACAAA         250

GGTGTGTGTG TGTGTGTGTG TGTGTGCATG CACAGCAAGA CGGAGAGGGA         300

GTTCTGGAAG GCAGCCAACG TGAGTTCCAT AGGGACCTGC TATTTCCTAG         350

CTCAGATCTC AGTGTTCTTG ACTATAAAAT GGGGACACCC ACCTTGGAGT         400

GGTTGTTAAT AAGACACTTG AACGCAGAAC CTAGCACCTC AGATT             445

(2) INFORMATION FOR SEQ ID NO:19:

(i) SEQUENCE CHARACTERISTICS:
            (A) LENGTH: 401 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:19:

CACCAACGCT TCCTGTATGG GCTTCCTGGA GAGGATCAGG AGGAGGGGAG         50

GACCTCGGGA TGAACTCCCA CCAGGGCCTG GCCACGGGTG GGATGAGTGA         100

CCACAGTGGC CTGCCAGACA AGGGTGTGTG TGTGTGTGTG TGTGTGTGTG         150

TGTGTGCATG CACAGCAAGA TGGAGAGGGA GTTCACGGGT GGGATGAGTG         200

GGCACAGTGG CCTGCCAGAC AAGGGTGTGT GTGTGTGTGC ACGCACAGCA         250

AGATGGACAG GGAATTTTGG AAGCCGGCCA AGCCATAGGG ACCTGCTATT         300

TCCTAGCTCA GATCTCGGTA TTCTTGAGTA TTAAATGGGG ACACCTACCT         350

TGCAATGGTT GTAAATAAGA CACTTGAACG CAGAGCCTAG CACTTCAGAT         400

T                                                             401

(2) INFORMATION FOR SEQ ID NO:20:

(i) SEQUENCE CHARACTERISTICS:
            (A) LENGTH: 344 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:20:

TCCCACCAAC GCTTCCTGTA TGGGCTTCCT GAAGAGGATC AGGAGAAGGG         50

GAGGACCTCA GGATGAGCTC CCACCAGGGC CTGGCCACGG GTGGAATGAG         100

TGGGCACAGT GGCCTGCCAG ACAAGGGTGT GTGTGTGTAT GTGTGTGTGT         150

GTGTGTGTGT GTGTGTGCGC GCTCACCCAC AACAAGACGG AGAGGGAGTT         200

CTGGAAGCCG GACAACGTGA GTTCCATAGG GACCTGCTGT TTCCTAGCTC         250

AGATCTCAGT GTTCTTGATT ATAAAATGGG GACACCTACC TTGCAACGGT         300

TGTAAATAAG ACACATTGGA ACGCAGAGGC TAGCACTTCA GATT              344

(2) INFORMATION FOR SEQ ID NO:21:

(i) SEQUENCE CHARACTERISTICS:
            (A) LENGTH: 349 base pairs
            (B) TYPE: nucleic acid
            (C) STRANDEDNESS: single
            (D) TOPOLOGY: linear (ii) MOLECULE TYPE: DNA
```

(xi) SEQUENCE DESCRIPTION: SEQ ID NO:21:

| | |
|---|---|
| TCCCACCAAC GCTTCCTGTA TGGGCTTCCT GAAGAGGATC AGGGAGAATG | 50 |
| GGAGGACCTC AGGATGAGCT CCCACCAGGA CCCTGCCACG GGTGGGATGA | 100 |
| GTGGGCACAG TGGCCTGCCA GACAAGGGTG TGTGTGTGTG TGTGTGTGTG | 150 |
| TGTGTGTGTG CGCGCGCGCG CGCGAGCGCT CACACACAGC AAGACAGAGA | 200 |
| GGGAGTTCTG GAAGCCGGAC GACGTGAGTT CCATAGGGAC CTGCTGTTTC | 250 |
| CTAGCTCATT CTTCACTATA AATGGGGAC ACCTACCTTG CAATGGTTGT | 300 |
| AAATAAGAGT AAATAAGACA CTTGAATGCA GAGCCTAGCA CTTCAGATT | 349 |

(2) INFORMATION FOR SEQ ID NO:22:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

| | |
|---|---|
| TCCCACCAAC GCTTCCTGTA TGGGCTTCCT GAAGAGGATC AGGAGAATGG | 50 |
| GAGGACCTCG GGATGAGCTC CCACCAGGAC CCGGCCACGG GTGGGATGAG | 100 |
| TGGGCACAGT GGCCTGCCAG ACAAGGGTGT GTGTGTGTGT GTGTGTGTGT | 150 |
| GTGTGTGTGT GTGTGCGCGC GCGCGCGCTC ACACACAGCA AGACAGAGAG | 200 |
| GGAGTTCTGG AAGCAGGACG ACGTGAGTTC CATAGGGACC TGCTGTTTCC | 250 |
| TAGCTCAGAT CTCAGTGTTC TTCACTATAA AATGGGACA CCTACCTTGC | 300 |
| AATGGTTGTA AATAAGACAC TTGAATGCAG AGCCTAGCAC TTCAGATT | 348 |

(2) INFORMATION FOR SEQ ID NO:23:

(i) SEQUENCE CHARACTERISTICS:
        (A) LENGTH: 344 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

| | |
|---|---|
| TCCCACCAAC GCTTCCTGTA TGGGCTTCCT GAAGAGGATC AGGAGAATGG | 50 |
| GAGGACCTCG GGATGAGCTC CCACCAGGAC CCGGCCACGG GTGGGATGAG | 100 |
| TGGGCACAGT GGCCTGCCAG ACAAGGGTGT GTGTGTGTGT GTGTGTGTGT | 150 |
| GTGTGTGTGT GCGCGCGCGC GCGCTCACAC ACAGCAAGAC AGAGAGGGAG | 200 |
| TTCCGGAAGC CGGACGACGT GAGTTCCATA GGGACCTGCT GTTTCCTAGC | 250 |
| TCAGATCTCA GTGTTCTTCA CTATAAAATG GGGACACCTA CCTTGCAATG | 300 |
| GTTGTAAATA AGACACTTGA ATGCAGAGCC TAGCACTTCA GATT | 344 |

(2) INFORMATION FOR SEQ ID NO:24:

(i) SEQUENCE CHARACTERISTICS:
        (A) LENGTH: 326 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

TCCCACCAAC GCTTCCTGTA TGGGCTTCCT GAAGAGGATC AGGAGAATGG         50

GAGGACCTCG GGATGAGCTC CCACCAGGGC CCGGCCACGG GTGGGATGAG        100

TGGGCACAGT GGCCTGCCAG ACAAGGGGGT GTGTGTGTGT GTGTGCACGC        150

GCGCGCTCAC ACACAGCAAG ACAGAGAGGG AGTTCTGGAA GCAGGACGAC        200

GTGAGTTCCA TAGGGACCTG CTGTTTCCTA GCTCAGATCT CAGTGTTCTT        250

CACTATAAAA TGGGGACACC TACCTTGCAA TGGTTGTAAA TAAGACACTT        300

GAACGCAGAG CCTAGCACTT CAGATT                                  326

(2) INFORMATION FOR SEQ ID NO:25:

(i) SEQUENCE CHARACTERISTICS:
            (A) LENGTH: 308 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:25:

TCCCACCAAC GCTTCCTGTA TGGGCTTCCT GAAGAGGATC AGGAGAGGGG         50

GAGGACCTCA GGATGAGCTC CCACCAGGGC CTGGCCACGG GTGGGATGAG        100

TGGGCACAGT GGCCTGCCAG ACAAGGGTGT GTGTGTGGTC ACCCACAGCA        150

AGACGGAGAG GGAGTTCTGG AAGCCGGACA ACGTGAGTTC CATAGGGACC        200

TGCTGTTTCC TAGCTCAGAT CTCAGTGTTC TTGACTATAA AATGGGGACA        250

CCTACCTTGC AATGGTTGTA AATAAGACAC TTGAACGCAG AGCCTAGCAC        300

TTCAGATT                                                     308

(2) INFORMATION FOR SEQ ID NO:26:

(i) SEQUENCE CHARACTERISTICS:
            (A) LENGTH: 308 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:26:

TCCCACCAAC GCTTCCTGTA TGGGCTTCCT GAAGAGGATC AGGAGAGGGG         50

GAGGACCTCG GGATGAGCTC CCACCAGGGC CTGGCCACAG GTGGGATGAG        100

TGGGCACAGT GGCTTGCCAG ACAAGGGTGT GTGTGTGGTC ACCCACAGCA        150

AGACGGAGAG GGAGTTCTGG AAGCCGGACA ACGTGAGTTC CATAGGGACC        200

TGCTGTTTCC TAGCTCAGAT CTCAGTGTTC TTGACTATAA AATGGGGACA        250

CCTACCTTGC AATGGTTGTA AATAAGACAC TAGAACGCAG AGCCTAGCAC        300

TTCAGATT                                                     308

(2) INFORMATION FOR SEQ ID NO:27:

(i) SEQUENCE CHARACTERISTICS:
            (A) LENGTH: 329 base pairs
            (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:27:

```
TCCCACCAAC GCTTCCTGTA TGGGCTTCCT GGAGAGGATC AGGAGGAGGG          50

GAGGACCTCG GGATGAACTC CCACCAGGGC CCGGCCACGG GTGGGATGAG         100

TGACCACAGT GGCCTGCCAG ACAAGGGTGT GTGTGTGTGT GTGTGTGTGT         150

GTCTGTGTGT GTGCGCGCGC ACACAGCAAG ATGGAGAGGG AATTCTGGAA         200

GCCGGCCAAG CCATAGGAGC CTGCTATTTC CTAGCTCAGA TCTTGGTATT         250

CTTGAGTATT AACTGGGGAC ACCTACCTTG CAATGGTTGT AAATAAGACA         300

CTTGAACGCA GAGCCTAGCA CTTCAGATT                                329
```

(2) INFORMATION FOR SEQ ID NO:28:

(i) SEQUENCE CHARACTERISTICS:
        (A) LENGTH: 548 amino acids
        (B) TYPE:AMINO
        (B) TYPE:AMINO
        (C) STRANDEDNESS: single
        (D) TOPOLOGY: linear (ii) MOLECULE TYPE: peptide (xi) SEQUENCE DESCRIPTION: SEQ ID NO:28:

```
Met  Ser  Gly  Asp  Thr  Gly  Pro  Pro  Lys  Gln
                    5                        10

Gly  Gly  Thr  Arg  Tyr  Gly  Ser  Ile  Ser  Ser
                    15                       20

Pro  Pro  Ser  Pro  Glu  Pro  Gln  Gln  Ala  Pro
                    25                       30

Pro  Gly  Gly  Thr  Tyr  Leu  Ser  Glu  Lys  Ile
                    35                       40

Pro  Ile  Pro  Asp  Thr  Glu  Ser  Gly  Thr  Phe
                    45                       50

Ser  Leu  Arg  Lys  Leu  Trp  Ala  Phe  Thr  Gly
                    55                       60

Pro  Gly  Phe  Leu  Met  Ser  Ile  Ala  Phe  Leu
                    65                       70

Asp  Pro  Gly  Asn  Ile  Glu  Ser  Asp  Leu  Gln
                    75                       80

Ala  Gly  Ala  Val  Ala  Gly  Phe  Lys  Leu  Leu
                    85                       90

Trp  Val  Leu  Leu  Trp  Ala  Thr  Val  Leu  Gly
                    95                       100

Leu  Leu  Cys  Gln  Arg  Leu  Ala  Ala  Arg  Leu
                    105                      110

Gly  Val  Val  Thr  Gly  Lys  Asp  Leu  Gly  Glu
                    115                      120

Val  Cys  His  Leu  Tyr  Tyr  Pro  Lys  Val  Pro
                    125                      130

Arg  Ile  Leu  Leu  Trp  Leu  Thr  Ile  Glu  Leu
                    135                      140

Ala  Ile  Val  Gly  Ser  Asp  Met  Gln  Glu  Val
                    145                      150
```

```
            Ile Gly Thr Ala Ile Ala Phe Ser Leu Leu
                            155                 160

Ser Ala Gly Arg Ile Pro Leu Trp Gly Gly
                            165                 170

Val Leu Ile Thr Ile Val Asp Ala Phe Phe
                            175                 180

Phe Leu Phe Leu Asp Asn Tyr Gly Leu Arg
                            185                 190

Lys Leu Glu Ala Phe Phe Gly Phe Leu Ile
                            195                 200

Thr Ile Met Ala Leu Thr Phe Gly Tyr Glu
                            205                 210

Tyr Val Val Ala Gln Pro Ala Gln Gly Ala
                            215                 220

Leu Leu Gln Gly Leu Phe Leu Pro Ser Cys
                            225                 230

Pro Gly Cys Gly Gln Pro Glu Leu Leu Gln
                            235                 240

Ala Val Gly Ile Ile Gly Ala Ile Ile Met
                            245                 250

Pro His Asn Ile Tyr Leu His Ser Ser Leu
                            255                 260

Val Lys Ser Arg Glu Val Asp Arg Ser Arg
                            265                 270

Arg Ala Asp Ile Arg Glu Ala Asn Met Tyr
                            275                 280

Phe Leu Ile Glu Ala Thr Ile Ala Leu Ser
                            285                 290

Val Ser Phe Leu Ile Asn Leu Phe Val Met
                            295                 300

Ala Val Phe Gly Gln Ala Phe Tyr Lys Gln
                            305                 310

Thr Asn Gln Ala Ala Phe Asn Ile Cys Ala
                            315                 320

Asn Ser Ser Leu Gln Asp Tyr Ala Pro Ile
                            325                 330

Phe Pro Arg Asn Asn Leu Thr Val Ala Val
                            335                 340

Asp Ile Tyr Gln Gly Gly Val Ile Leu Gly
                            345                 350

Cys Leu Phe Gly Pro Ala Ala Leu Tyr Ile
                            355                 360

Trp Ala Val Gly Leu Leu Ala Ala Gly Gln
                            365                 370

Ser Ser Thr Met Thr Gly Thr Tyr Ala Gly
                            375                 380

Gln Phe Val Met Glu Gly Phe Leu Lys Leu
                            385                 390

Arg Trp Ser Arg Phe Ala Arg Val Leu Leu
                            395                 400

Thr Arg Ser Cys Ala Ile Leu Pro Thr Val
                            405                 410
```

```
Leu  Leu  Ala  Val  Phe  Arg  Asp  Leu  Arg  Asp
               415                      420

Leu  Ser  Gly  Leu  Asn  Asp  Leu  Leu  Asn  Val
               425                      430

Leu  Gln  Ser  Leu  Leu  Leu  Pro  Phe  Ala  Val
               435                      440

Leu  Pro  Ile  Leu  Thr  Phe  Thr  Ser  Met  Pro
               445                      450

Ala  Leu  Met  Arg  Glu  Phe  Ala  Asn  Gly  Leu
               455                      460

Val  Ser  Lys  Val  Ile  Thr  Ser  Ser  Ile  Met
               465                      470

Val  Leu  Val  Cys  Ala  Val  Asn  Leu  Tyr  Phe
               475                      480

Val  Ile  Ser  Tyr  Val  Pro  Ser  Leu  Pro  His
               485                      490

Pro  Ala  Tyr  Phe  Ser  Leu  Val  Ala  Leu  Leu
               495                      500

Ala  Ala  Ala  Tyr  Leu  Gly  Leu  Thr  Thr  Tyr
               505                      510

Leu  Val  Trp  Thr  Cys  Leu  Ile  Thr  Gln  Gly
               515                      520

Ala  Thr  Leu  Leu  Ala  His  Ser  Ser  His  Gln
               525                      530

Arg  Phe  Leu  Tyr  Gly  Leu  Pro  Glu  Glu  Asp
               535                      540

Gln  Glu  Lys  Gly  Arg  Thr  Ser  Gly
               545
```

(2) INFORMATION FOR SEQ ID NO:29:

(i) SEQUENCE CHARACTERISTICS:
        (A) LENGTH: 587 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

```
GGGCTTCCTG AAGAGGATCA GGAGAAGGGG AGGACCTCGG GGATGAGCTC        50

CCACCAGGGC CTGGCCACGG GTGGGATGAG TGGGCACAGT GGCCTGTCAG       100

ACAAGGGTGT GTGTGTGTGT GTGTGTGTGT GTGAAGGCAG CAAGACAGAG       150

ACGGAGTTCT GGAAGCTGGC CAACGTGAGT TCCAGAGGGA CCTGTGTGTG       200

TGTGTGTGAC ACACTGGCCT GCCAGACAAG GGTGTGTGTG TGTGTGTGTG       250

TGTGTGTGTG TGTGCATGCA CAGCAAGACA GAGAGGGAGT TCTGGAAGCC       300

AGCCAACGTG AGTTCCATAG GGACCTGCTA TTTCCTAGCT CAGATCTCAG       350

TGTTCTTGAC TATAAAATGG GGACACCTAC CTTGGAATGG TTGTAAATAA       400

GACACTTGAA CGCAGAGCCT AGCACTTCAG ATTTAAAAAC AAAAGAATCA       450

TAATTCCAAA AGTTACTGAG CACTATCACA GGAGTGACCT GACAGACCCA       500

CCCAGTCCAG GGTGGGACCC AGGCTCCAAA CTGATTTAAA ATAAGAGTCT       550

GAAAATGCTA AATAAATGCT GTTGTGCTTA GTCCCCG                     587
```

(2) INFORMATION FOR SEQ ID NO:30:

(i) SEQUENCE CHARACTERISTICS:
        (A) LENGTH: 585 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

```
GGGCTTCCTG AAGAGGATCA GGAGAAGGGG AGGACCTCGG GGATGAGCTC            50

CCACCAGGGC CTGGCCACGG GTGGGATGAG TGGGCACAGT GGCCTGTCAG           100

ACAAGGGTGT GTGTGTGTGT GTGTGTGTGT GAAGGCAGCA AGACAGAGAC           150

GGAGTTCTGG AAGCTGGCCA ACGTGAGTTC CAGAGGGACC TGTGTGTGTG           200

TGTGTGACAC ACTGGCCTGC CAGACAAGGG TGTGTGTGTG TGTGTGTGTG           250

TGTGTGTGTG TGCATGCACA GCAAGACAGA GAGGGAGTTC TGGAAGCCAG           300

CCAACGTGAG TTCCATAGGG ACCTGCTATT TCCTAGCTCA GATCTCAGTG           350

TTCTTGACTA TAAAATGGGG ACACCTACCT TGGAATGGTT GTAAATAAGA           400

CACTTGAACG CAGAGCCTAG CACTTCAGAT TTAAAAACAA AAGAATCATA           450

ATTCCAAAAG TTACTGAGCA CTATCACAGG AGTGACCTGA CAGACCCACC           500

CAGTCCAGGG TGGGACCCAG GCTCCAAACT GATTTAAAAT AAGAGTCTGA           550

AAATGCTAAA TAAATGCTGT TGTGCTTAGT CCCCG                           585
```

(2) INFORMATION FOR SEQ ID NO:31:

(i) SEQUENCE CHARACTERISTICS:
        (A) LENGTH: 149 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

```
GTGTGTGTGT GTGTGTGTGT ATGTGTGTNN NNNNNNNNNN NNNNNNNNNN            50

NNNNNNNNNN NNNNNNNNNN NNNNNNNNNN NNNNNNNNNG TGTGTGTGTN           100

NNNNNNNNNN NNNNNNNNNN NNNGTGTGTG TGTGTGTGTG TGTGTGTGT            149
```